(12) United States Patent
DiMeo, Jr. et al.

(10) Patent No.: US 6,596,236 B2
(45) Date of Patent: *Jul. 22, 2003

(54) MICRO-MACHINED THIN FILM SENSOR ARRAYS FOR THE DETECTION OF $H_2$ CONTAINING GASES, AND METHOD OF MAKING AND USING THE SAME

(75) Inventors: Frank DiMeo, Jr., Danbury, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/828,115

(22) Filed: Apr. 6, 2001

(65) Prior Publication Data

US 2002/0017126 A1 Feb. 14, 2002

Related U.S. Application Data

(63) Continuation-in-part of application No. 09/231,277, filed on Jan. 15, 1999, now Pat. No. 6,265,222.

(51) Int. Cl.[7] .................................................. G01N 7/00
(52) U.S. Cl. ........................ 422/88; 436/144; 436/147; 73/23.2; 73/31.06
(58) Field of Search ................................ 436/144, 147, 436/148; 422/83, 88, 90, 91, 98; 73/23.2, 31.06

(56) References Cited

U.S. PATENT DOCUMENTS

| 3,732,076 A | 5/1973 | Toy et al. | |
| 3,768,975 A | 10/1973 | Toy | 23/253 |
| 3,951,603 A | 4/1976 | Obayashi et al. | 23/232 |
| 3,953,173 A | 4/1976 | Obayashi et al. | 23/232 |
| 4,058,368 A | 11/1977 | Svensson et al. | 23/254 E |
| 4,338,281 A | 7/1982 | Treitinger et al. | |
| 4,892,834 A | 1/1990 | Rauh | 436/149 |
| 4,953,387 A | 9/1990 | Johnson et al. | 73/25.03 |

(List continued on next page.)

OTHER PUBLICATIONS

J.N. Huiberts, et al., "Yttrium and Lanthanum Hydride Films with Switchable Optical Properties", *Nature*, 1996, vol. 380, pp. 231–234.

(List continued on next page.)

*Primary Examiner*—Lyle A. Alexander
(74) *Attorney, Agent, or Firm*—Steven J. Hultquist; William Ryann

(57) ABSTRACT

The present invention provides a hydrogen sensor including a thin film sensor element formed by metal organic chemical vapor deposition (MOCVD) or physical vapor deposition (PVD), on a micro-hotplate structure. The thin film sensor element includes a film of a hydrogen-interactive metal film that reversibly interacts with hydrogen to provide a correspondingly altered response characteristic, such as optical transmissivity, electrical conductance, electrical resistance, electrical capacitance, magneto resistance, photoconductivity, etc., relative to the response characteristic of the film in the absence of hydrogen. The hydrogen-interactive metal film may be overcoated with a thin film hydrogen-permeable barrier layer to protect the hydrogen-interactive film from deleterious interaction with non-hydrogen species. The hydrogen permeable barrier may comprise species to scavenge oxygen and other like species. The hydrogen sensor of the invention may be usefully employed for the detection of hydrogen in an environment susceptible to the incursion or generation of hydrogen and may be conveniently configured as a hand-held apparatus.

43 Claims, 13 Drawing Sheets

U.S. PATENT DOCUMENTS

| | | | |
|---|---|---|---|
| 5,211,053 A | 5/1993 | Nolting et al. | 73/31.05 |
| 5,279,795 A | 1/1994 | Hughes et al. | 422/98 |
| 5,345,213 A | 9/1994 | Semancik | 338/34 |
| 5,356,756 A | 10/1994 | Cavicchi et al. | 430/315 |
| 5,417,821 A | 5/1995 | Pyke | 204/153.1 |
| 5,520,753 A | 5/1996 | Hunter | 148/430 |
| 5,545,300 A | 8/1996 | Yun et al. | 204/424 |
| 5,635,729 A | 6/1997 | Griessen et al. | 257/2 |
| 5,652,433 A | 7/1997 | Ouwekerk et al. | 257/1 |
| 5,659,127 A | 8/1997 | Shie et al. | 73/31.05 |
| 5,668,301 A | 9/1997 | Hunter | 73/23.2 |
| 5,670,115 A | 9/1997 | Cheng | 422/90 |
| 5,733,506 A | 3/1998 | Silver et al. | 422/90 |
| 5,783,152 A | 7/1998 | Nave | 422/82.06 |
| 6,006,582 A | 12/1999 | Bhandari et al. | |
| 6,109,094 A | 8/2000 | Baranzahi et al. | |

OTHER PUBLICATIONS

Ahuja, R.; Johansson, B.; Wills, J.M.; Eriksson, O. "On the Semiconducting State and Structural Properties of $YH_3$ from First Principles Theory" *Appl. Phys. Lett.*, 1997, vol. 71, No. 24, pp. 3498–3500.

Freemantle, M., "Hydride Fims Display Mirror–Window Changes", *C&EN*, 1996, p. 9.

S. Semancik et al., "Selected–area depostioin of multiple active films for cunductometric microsensor arrays," The $8^{th}$ Int. Conf. On Solid State Sensors and actuators and Eurosensors IX, Stockholm, Sweeden, Jun. 25–29, 1995, pp. 831–834.

S. Majoo et al., "A selected–area CVD methhold for deposition of sensing films in minilithically integrated gas detectors" IEEE Electron Device Letters, vol. 16, 1995, pp. 217–219.

J.S. Suehle, et al., "Tin oxide gas sensor fabricated using CMOS micro–hotplates and in situ processing," IEEE Electron Device Lett., vol. 14, 1993, pp. 118–120.

Semancik et al., "The use of surface and thin film science in the development of advanced gas sensors," Appl. Surf. Sci., vol. 70. 1993, pp. 337–346.

R.E. Cavicchi, et al., "Fast temperature programmed sensing for microhotplate gas sensors," IEEE Electron Device Letters, vol. 16, 1995, pp. 286–288.

R.E. Cavicchi, et al., "Growth of $SnO_2$ films on micromachined hotplates," Appl. Phys. Lett., vol. 66, 1995, pp. 812–814.

C.L. Johnson et al., "Integrated ultra–thin film gas sensors," Sensors and Actuators B, vol. 20, 1994, pp. 55–62.

X. Wang et al., "Monolithic thin film metal oxide gas sensor arrays with application to moniitoring of organic vapors," Sensors and Actuators B, vol. 28, 1995, pp. 63–70.

N.R. Swart et al., "Design optimization of integrated micro–hotplates," Sensors and Actuators A, vol. 43, 1994, pp. 3–10.

N. Najafi, et al., "A micromachined thin film gas sensor," IEEE Electron Device Lett., vol. 41, (10) 1994.

A. Setkus, et al., "The Room Temperature Ammonia Sensor Based on Improved $Cu_xS$–Porous–Si Structure", Eurosensor XIV, ISBN 87–89935–50–0, p. 927–930.

J. Marshall et al., Report NO. NISTIR 5402, 1994.

F. DiMeo Jr., et al., "In situ conductivity characaterization of oxide thin film growth phenomena on microhotplates," J. Vac. Sci. Tech. A, vol. 16, 1998, pp. 131–138.

F. DiMeo Jr. et al., "MOCVD of $SnO_2$ on silicon microhotplate arrays for use in gas sensing application," Mater. Res. Soc. Symp. Proc. vol. 415, 1996, pp. 231–236.

F. DiMeo Jr. et al., "Silicon microhotplate arrays as a platform for efficient gas sensing thin film research," Mat. Res. Soc. Symp. Proc., 1997, p. 444.

F.J.A. den Broeder, et al., "Visualization of hydrogn migration in solids using switchable mirrors," Nature vol. 394, 1998, pp. 656–658.

Van der Sluis, et al., "Optical weitches based on magnesium lanthanide alloy hydriides," Appl. Phys. Lett., vol. 70, 1997, pp. 3356–3358.

J.N. Huiberts et al., Logrithmic divergence of the electrical resistivity in the metal hydride YH3–d, Physical Review Letters, vol. 79, 1997, pp. 3724–3727.

Mihaela Ghita, et al., "Microelectronic Manufacturing of a Microsensor Based on Polyaniline for Ammonia Gas Sensing", Proc. $22^{nd}$ Intl. Conference on Microelectronics (MIEL 2000), vol. 2, NIS, SERBIA, May 14–17, 2000.

S.A. Krutovertsev, et al., "Polymer film–based sensor for ammonia detection", Sensors and Actuators B. 7 (1992), 492–494.

Final Technical Report for NASA Supported Contract No. NAS8–98188 for Phase I–Research Program Entitled "Microhotplate Based Palladium–Coated Metal Hydride Thin Film Hydrogen Sensor Arrays" for Contract Period from Mar. 13, 1998 to Sep. 12, 1998.

MICRO-MACHINED THIN FILM SENSOR ARRAYS FOR THE DETECTION OF H₂ CONTAINING GASES, AND METHOD OF MAKING AND USING THE SAME

RELATED APPLICATIONS

This application is a continuation-in-part application to U.S. patent application, Ser. No. 09/231,277, filed on Jan. 15, 1999, now U.S. Pat. No. 6,265,222 entitled "MICRO-MACHINED THIN FILM HYDROGEN GAS SENSOR, AND METHOD OF MAKING AND USING THE SAME." Additionally, this patent application hereby incorporates by reference U.S. patent application, Ser. No. 09/231,277, filed on Jan. 15, 1999, now U.S. Pat. No. 6,265,222 entitled "MICRO-MACHINED THIN FILM HYDROGEN GAS SENSOR, AND METHOD OF MAKING AND USING THE SAME." The disclosures of the foregoing references are hereby incorporated herein by reference in their entireties, together with the disclosures of the following pending United States Patent Applications: U.S. patent application Ser. No. 09/042,698 filed Mar. 17, 1998, now U.S. Pat. No. 6,006,582 in the names of Gautam Bhandari and Thomas H. Baum for "Hydrogen Sensor Utilizing Rare Earth Metal Thin Film Detection Element, and Differential Optical Sensing Method for Detection of Hydrogen" and U.S. patent application Ser. No. 09/081,957 filed May 19, 1998 now U.S. Pat. No. 6,029,500 in the name of Glenn M. Tom for "Piezoelectric Quartz Crystal Hydrogen Sensor, and Hydrogen Sensing Method Utilizing Same."

FIELD OF THE INVENTION

The present invention relates to a micro-machined thin film gas sensor device, and a method of making and using the same. More specifically, the present invention relates to solid-state sensor arrays for the detection of $H_2$, $NH_3$, and sulfur containing gases.

BACKGROUND OF THE INVENTION

Hydrogen gas is used in variety of applications ranging from semiconductor thin film processing to rocket fuel in the aerospace industry. The combustible nature of hydrogen however, makes its detection vitally important. A common need in each of these and other similar technologies is the ability to detect and monitor gaseous hydrogen. Hydrogen gas sensors that quickly and reliably detect hydrogen over a wide range of oxygen and moisture concentrations are not currently available, and must be developed in order to facilitate the transition to a hydrogen based energy economy "Hydrogen will join electricity in the 21$^{st}$ Century as a primary energy carrier in the nation's sustainable energy future." (DOE 1995) This bold statement was made as part of the 1995 Hydrogen Vision and reflects the tremendous potential of hydrogen as an energy system. The abundance and versatility of hydrogen suggests that it can provide solutions to problems encountered with current fossil fuel energy systems, such as declining domestic supplies, air pollution, global warming, and national security.

Significant research and development efforts are currently underway to make the widespread use of hydrogen technically and economically feasible. These efforts are directed toward creating the basic building blocks of a hydrogen economy: production, storage, transport and utilization. An underlying need of each of these building blocks is the ability to detect and quantify the amount of hydrogen gas present. This is not only required for health and safety reasons, but will be required as a means of monitoring hydrogen based processes. For example, if hydrogen were to be introduced as an automobile fuel additive, several sensors would be needed to detect potential hydrogen gas leaks, as well as to monitor and provide feedback to regulate the air/fuel/hydrogen mixture.

Although the safety record of the commercial hydrogen industry has been excellent, it is estimated that undetected leaks were involved in 40% of industrial hydrogen incidents that did occur. Emerging hydrogen based energy systems will require hydrogen sensors that are as ubiquitous as computer chips have become in our factories, homes, and in our cars. This means that the ability to produce large volumes of sensors at a low cost is paramount.

In order to support an effective hydrogen detection and monitoring system, the hydrogen sensor element must fulfill several requirements. It needs to be selective to hydrogen in variety of atmospheres (including the oxygen-rich high-humidity environments found in fuel cells). It must have a good signal to noise ratio and a large dynamic range. Speed of detection is a critical requirement to ensure rapid response to potentially hazardous leaks. Long lifetimes between calibrations are desirable in order to minimize maintenance. Low power consumption is requisite for use in portable instrumentation and personnel monitoring devices. Ultimately, these must all be achieved by a safe sensor element that is affordable to manufacture in large numbers, so that safe design principles are the deciding factor in the number and locations of detection points.

Existing gas sensors are not adequate, either technically and/or from a cost standpoint. Issues such as size, thermal range, and lifetime have proven to be substantial hurdles for current technologies to overcome. Therefore, there is a need to address these issues, with the development of MEMS (Micro-Electro-Mechanical Systems) based solid-state sensor arrays for the detection of, $NH_3$, and sulfur containing gases.

Additionally, hydrogen-containing gases such as $CH_4$, $C_2H_6$, acetone, methanol etc. are used in large variety of industrial applications ranging from semiconductor thin film processing to petroleum and polymer manufacturing. The combustible nature of many of these gases as well as the always-increasing need for improved process control makes the detection and monitoring of these gases vitally important. Difficulties with the sensors that are currently used to detect these gases are that they are not chemically specific, and often will have similar response for different gases. In addition, many of these sensors are combustion based and rely on the presence of oxygen. Therefore, a need exists for a sensor with reproducible results specific to individual hydrogen containing gases, able to operate in environments with little to no oxygen present. Furthermore, a need exists for a gas sensor having no moving parts, a response time on the order of seconds, with minimal power consumption, and capable of being used in a hand held portable instrument About one-half of all the sensors used to measure hazardous gases measure hydrogen. The bulk of these systems utilize as the detector element a Group VIIIB metal element (Ni, Pd, Pt) that is heated to catalytically oxidize the hydrogen, with the resulting change in heat load being the measured parameter for determination of the presence of hydrogen.

Sensors of such "hot wire" type have cross-sensitivity to other easily oxidized materials, such as alcohols and hydrocarbons. Such easily oxidized materials are common components of gases in a semiconductor-manufacturing environment, and in such application the result is frequent occurrence of false alarms.

Since the current generation of hot wire sensors require an oxidation reaction for operation, such sensors are unable to detect hydrogen when it is present in inert gas streams or environments, which are not of a character to support oxidative reaction. This is a severe deficiency of such hot wire sensors and limits their applicability and utility.

It would be a significant advance in the art to provide a sensor overcoming the aforementioned deficiencies of current hot wire sensors.

Another class of sensors includes metal-insulator semiconductor (MIS) or metal-oxide-semiconductor (MOS) capacitors and field effect transistors, as well as palladium-gated diodes. In general however, these sensors are limited to detecting low concentrations of hydrogen.

Because hydrogen is used in such a wide variety of environments, it is desirable to have a sensor that will be reproducible and specific to hydrogen, even with varying concentration of background gases such as oxygen, water and other contaminants.

It is also desirable to have a solid state sensor that has no moving parts, has a response time on the order of seconds, would operate with minimum power consumption, does not require frequent calibration, and could be used in a hand-held portable instrument.

It therefore is one object of the present invention to provide an improved hydrogen sensor.

It is another object of the invention to provide a hydrogen sensor that senses the presence of hydrogen in a reproducible and hydrogen-specific manner.

It is another object of the invention to provide a hydrogen sensor that senses the presence of hydrogen in a reproducible and hydrogen-specific manner, even with varying concentration of background gases such as oxygen, water and other contaminants.

It is yet another object of the present invention to provide a solid state hydrogen sensor that has no moving parts, has a response time on the order of seconds, operates with minimum power consumption, does not require frequent calibration, has a large dynamic detection range, and can be readily embodied as a hand-held portable instrument.

Other objects and advantages of the present invention will be more fully apparent from the ensuing disclosure and appended claims.

SUMMARY OF THE INVENTION

The present invention relates in one aspect to a hydrogen sensor, comprising a hydrogen-interactive thin film sensor element on a micro-hotplate structure.

The hydrogen-interactive thin film sensor element of such sensor may comprise a hydrogen-interactive thin film (i) arranged for exposure to an environment susceptible to the incursion or generation of hydrogen and (ii) exhibiting a detectable change of physical property when the hydrogen-interactive thin film is exposed to hydrogen. Such detectable change of physical property may comprise optical transmissivity, electrical resistivity, electrical conductivity, electrical capacitance, magneto-resistance, photoconductivity, and/or any other detectable property change accompanying the exposure of the thin film sensor element to hydrogen. The hydrogen sensor may further include a detector constructed and arranged to convert the detectable change of physical property to a perceivable output, e.g., a visual output, auditory output, tactile output, and/or auditory output.

In one embodiment of the present invention these sensors couple novel thin films as the active layer with a MEMS structure known as a Micro-Hotplate. This coupling results in a $H_2$ gas sensor that has several unique advantages in terms of speed, sensitivity, stability and amenability to large-scale manufacture. Results indicate that this technology has substantial potential for meeting the sensing requirements of a hydrogen based energy economy.

In another embodiment, the hydrogen-interactive thin film is overlaid by a hydrogen-permeable material protecting the rare earth metal thin film from deleterious interaction with non-hydrogen components of the environment being monitored, such as nitrogen, oxygen, ammonia, hydrocarbons, etc. The protective-over layer may include a metal such as Pd, Pt, Ir, Rh, Ag, Au, Co, and/or alloys thereof. However, these alloys may not be sufficient to prevent the rare earth films and their alloys from oxidizing over long time periods. There are several possible mechanisms for this. Oxygen and other like species can diffuse through the rare earth film or film grain boundaries. If this is the case, a thicker rare earth coating may represent a viable solution. However, this solution may result in decreased sensitivity and responsivity. Another possibility is that the rare earth film is embrittled with repeated hydrogen exposure, and failing with time due to the $\alpha$ to $\beta$ phase transformation of rare earth hydrides that occurs at a hydrogen concentration of ~2%. One solution is to suppress this phase transition in rare earth films such as palladium by alloying the rare earth film with suitable elements, such as silver, titanium, nickel, chromium, aluminum or other species known to those skilled in the art. In this manner, the long-term stability of the underlying coating can be improved.

The micro-hotplate structure in the sensor of the invention may be advantageously constructed and arranged for selectively heating the hydrogen-interactive thin film gas sensor element according to a predetermined time-temperature program, e.g., involving cyclic heating of the hydrogen-interactive thin film gas sensor element by the micro-hotplate structure.

The invention relates in another aspect to a hydrogen sensor device, comprising:
  a micro-hotplate structure;
  a hydrogen-interactive thin film gas sensor element on the micro-hotplate structure; and
  a detector for sensing a detectable change of physical property of the film in exposure to hydrogen and generating a correlative output indicative of hydrogen presence.

A power supply may be provided in such device and may be constructed and arranged for actuating the micro-hotplate structure during and/or subsequent to sensing the detectable change of physical property of the rare earth metal thin film in exposure to hydrogen, and/or for energizing the detector.

A further aspect of the invention relates to a method of fabricating a hydrogen sensor on a substrate, comprising:
  constructing on the substrate a micro-hotplate structure; and
  forming on the micro-hotplate structure a hydrogen-interactive thin film that in exposure to hydrogen exhibits a detectable change of at least one physical property, and wherein the hydrogen-interactive thin film is arranged to be heated by the micro-hotplate structure.

A still further aspect of the invention relates to a method of detecting hydrogen in an environment, comprising:

providing a hydrogen sensor device comprising a hydrogen-interactive thin film operatively coupled with a micro-hotplate structure for selective heating of the hydrogen-interactive thin film, with the hydrogen-interactive thin film being arranged for exposure to the environment and exhibiting a detectable change of physical property when the hydrogen-interactive thin film is exposed to hydrogen;

exposing the hydrogen-interactive thin film to the environment;

outputting said detectable change of physical property when the presence of hydrogen in the environment is detected; and selectively heating the hydrogen-interactive thin film by the micro-hotplate structure during and/or subsequent to detection of hydrogen in said environment, to enhance the performance of the hydrogen-interactive thin film for detection of hydrogen.

Other objects and advantages of the invention will be more fully apparent from the ensuing disclosure and claims.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DETAILED DESCRIPTION OF THE INVENTION

Embodiments of the present invention are illustrated in the FIGUREs, like numerals being used to refer to like and corresponding parts of the various drawings.

The present invention provides a hydrogen sensor including a thin film sensor element formed by metal organic chemical vapor deposition (MOCVD) or physical vapor deposition (PVD), on a micro-hotplate structure. The thin film sensor element includes a film of a hydrogen-interactive metal film that reversibly interacts with hydrogen to provide a correspondingly altered response characteristic, such as optical transmissivity, electrical conductance, electrical resistance, electrical capacitance, magneto resistance, photoconductivity, etc., relative to the response characteristic of the film in the absence of hydrogen. The hydrogen-interactive metal film may be overcoated with a thin film hydrogen-permeable barrier layer to protect the hydrogen-interactive film from deleterious interaction with non-hydrogen species. The hydrogen permeable barrier may comprise species to scavenge oxygen and other like species. The hydrogen sensor of the invention may be usefully employed for the detection of hydrogen in an environment susceptible to the incursion or generation of hydrogen and may be conveniently configured as a hand-held apparatus.

Figure 1:
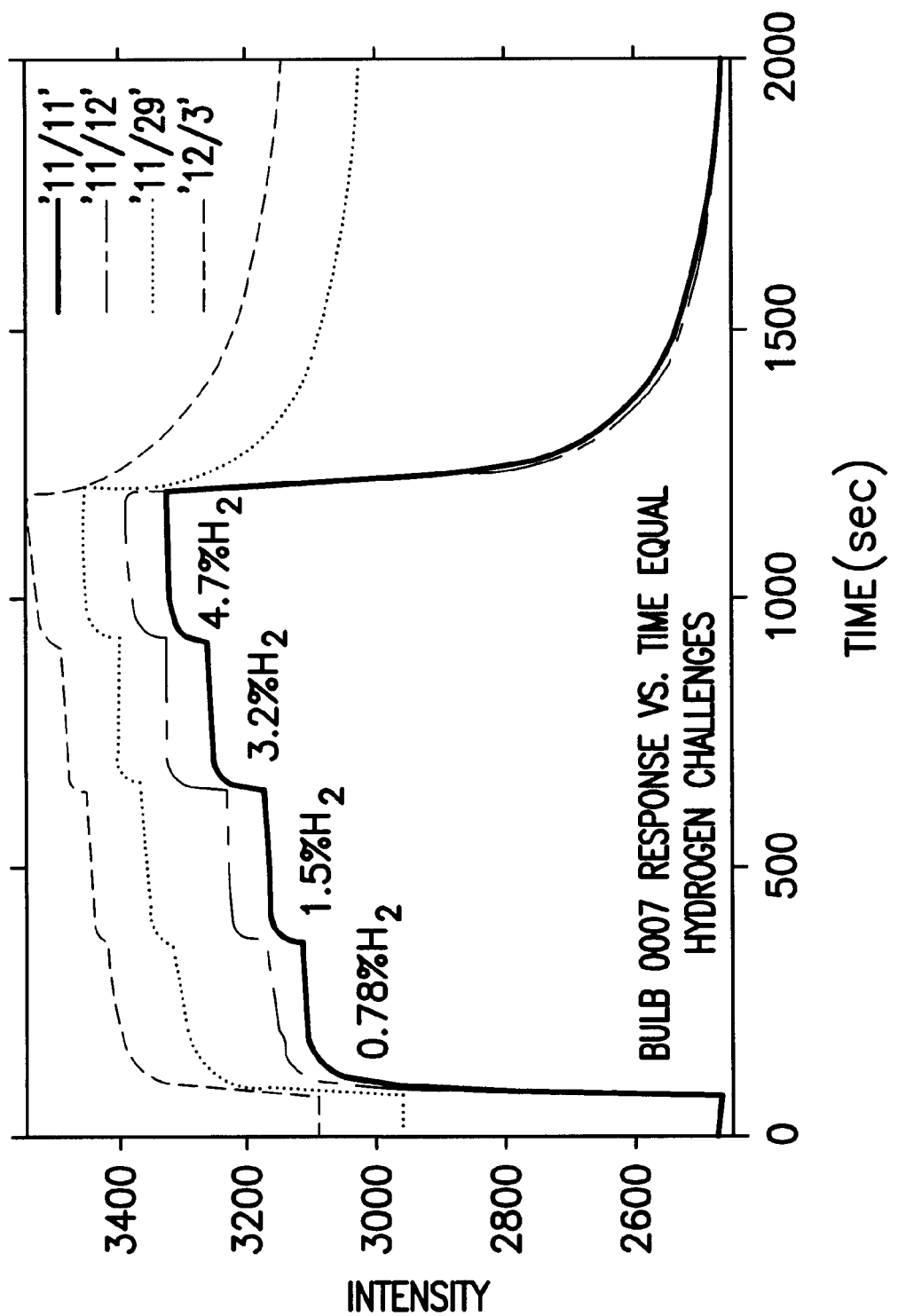
FIG. 1 plots long-term response behavior to hydrogen exposures as a function of time. Between each response shown was a continuous procession of similar exposures on a 50-minute period.

Stability is an important consideration in all sensor development efforts, and understanding the source and mechanism of instabilities and drift is vital for the development of useful devices. Through the useful life of many devices, decreases in the responsivity of the thin film devices are observed over time. This is illustrated in FIG. 1, which shows the response of a palladium coated yttrium film deposited on a miniature light bulb, taken over the coarse on one month.

Figure 2:
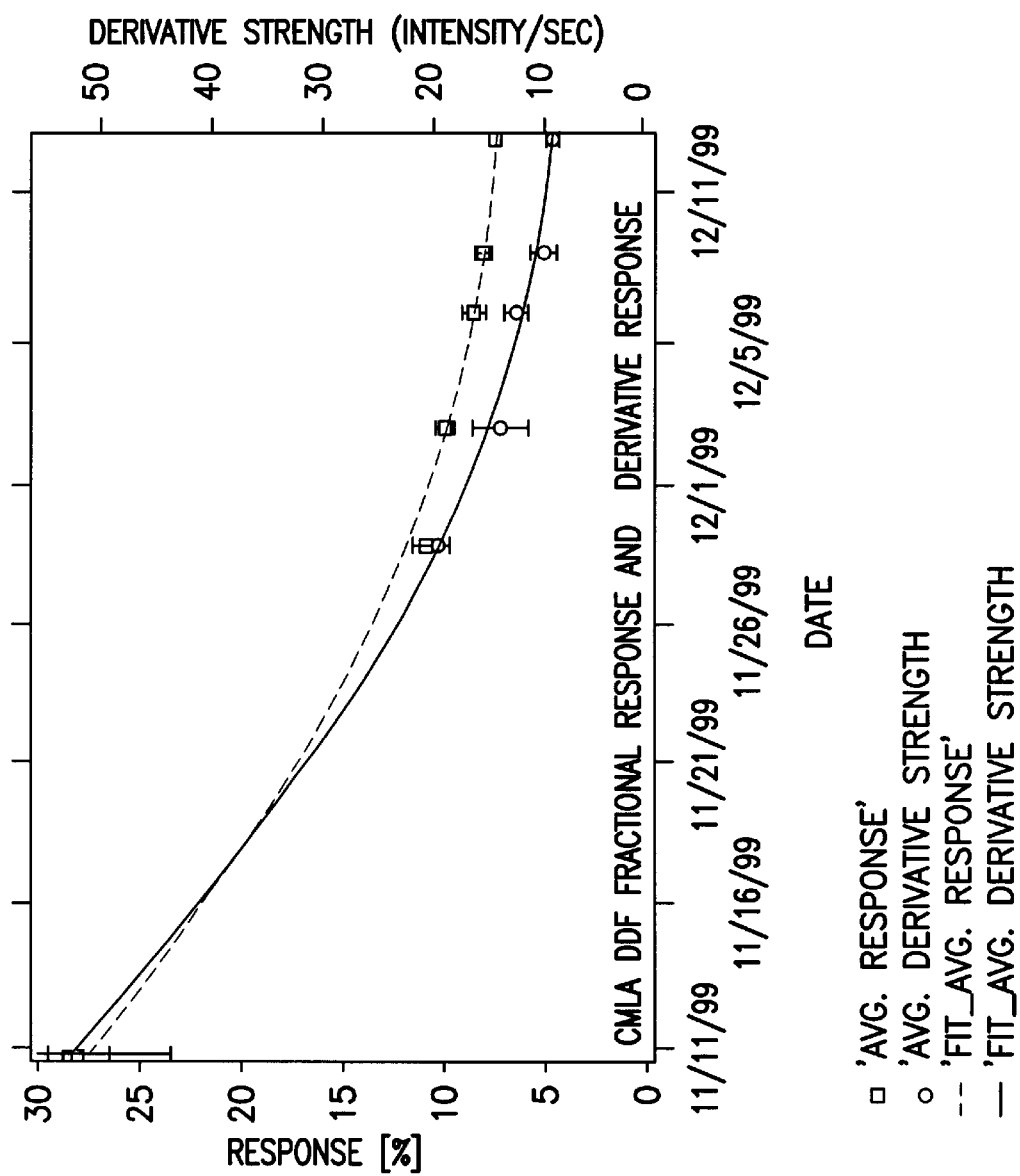
FIG. 2 plots the magnitude of response to hydrogen exposure as a function of date, from the data in FIG. 1. Both the fractional and derivative strength are plotted. Between each data point, the film was continuously exposed to hydrogen concentrations on a 50-minute period.

Between recorded observations, the film was continuously subjected to repeated hydrogen exposures on a 50-minute interval. This data was collected with a sensor system that utilizes a silicon photo diode. Over time, there is a monotonic increase in the baseline transmissivity as well as a decrease in the magnitude of the response as a function of hydrogen concentration. FIG. 2 quantifies those observations and plots the magnitude of response to 0.78% hydrogen exposure in air as a function of measurement date. The magnitude of response was calculated as the fraction of the base line, and as the strength of the derivative. (Both of these measurements are required for the accurate detection of hydrogen, as the derivative provides responses to rapid changes and concentration, and the change with respect to baseline would be required to detect slower concentration build ups.) Although the response for this sample has fallen off by a factor of 2 to 3 over the course of ~1 month, it appears that this decrease has leveled off and that there is still sufficient signal to noise present.

The present invention relates to a hydrogen sensor integrating a thin film hydrogen sensor element with a micro-hotplate structure. The hydrogen sensor of the invention is a solid-state device that may be adapted in a variety of apparatus embodiments to accommodate the objects of the invention. In one embodiment, the hydrogen-interactive thin film is overlaid by a hydrogen-permeable material protecting the rare earth metal thin film from deleterious interaction with non-hydrogen components of the environment being monitored, such as nitrogen, oxygen, ammonia, hydrocarbons, etc. The protective-over layer may include a metal such as Pd, Pt, Ir, Rh, Ag, Au, Co, and/or alloys thereof. However, these alloys may not be sufficient to prevent the rare earth films and their alloys from oxidizing over long time periods. One solution provided by the present invention is to suppress this phase transition in rare earth films such as palladium by alloying the rare earth film with suitable elements, such as silver, titanium, nickel, chromium, aluminum or other species known to those skilled in the art. In this manner, the long-term stability of the underlying coating can be improved.

Figure 3:
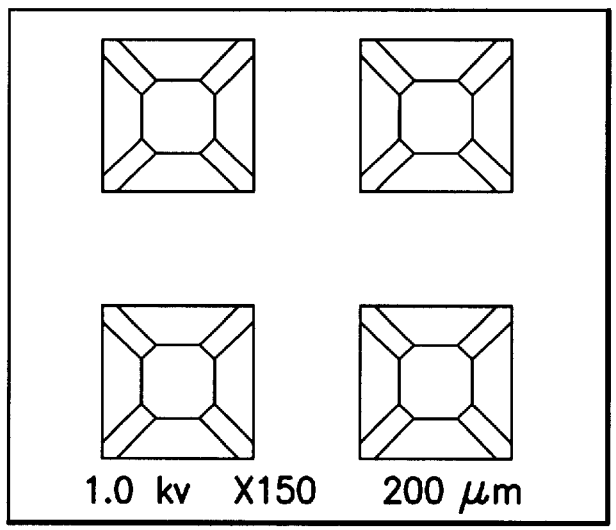
FIG. 3 is a scanning electron microscope (SEM) micrograph of a thin film sensor including a thin film sensor element deposited by metal organic chemical vapor deposition (MOCVD) on a micro-hotplate structure.

In the embodiment illustrated in FIG. 3, the rare earth film comprises a palladium alloy formed using single source e-beam deposition techniques. A 200-nm thick Y film 10 coated with a second film 12 comprising 120 nm of Pd and 30 nm of Ag at room temperature. The palladium was deposited in three steps, alternating with equal amounts of silver These films were subsequently annealed at different temperatures, and x-ray diffraction indicates that alloying occur at temperatures over 250° C. It seems that there is a significant thin film effect that results in alloying at temperatures that are well below the melting points of either metal.

The sensing mechanism of the hydrogen sensor device of the present invention is based on the reversible, hydrogen-induced transition from the metallic di-hydride compound to the semi-conducting tri-hydride compound, according to the following equation:

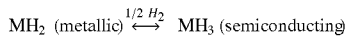

$$MH_2 \text{ (metallic)} \underset{}{\overset{1/2\,H_2}{\longleftrightarrow}} MH_3 \text{ (semiconducting)}$$

wherein M comprises the hydrogen-interactive thin film element. The hydrogen-interactive thin film element may comprise one or more thin films wherein at least one thin film is selected from the group consisting of rare earth metals, Group II elements or any combination thereof. The rare earth metal and the Group II element may be combined to form a Group II element doped rare earth metal thin film or an alloy thin film comprising the rare earth metal and the Group II element. Rare earth and alkaline earth hydride films are extremely oxophilic in nature, and may also interact with other atmospheric or environmental species in a manner that masks the hydrogen interaction. In order to obviate such deleterious interactions with non-hydrogen species, where the hydrogen sensor is intended to operate in environments containing same, it may be advantageous to overcoat the hydrogen-interactive thin film of the sensor with a protective film layer of a coating that is permeable to hydrogen, but is impermeable to the deleterious interaction species present in the environment. One such protective film layer material is palladium (Pd). Hydrogen is known to diffuse readily through a Pd film, while oxygen and nitrogen do not readily penetrate the Pd film, thus allowing the formation of the rare earth metal and/or Group II hydride without the formation of oxides and/or nitrides. Furthermore, it may be advantageous to incorporate scavenging components within the protective film layer 12 in order to obviate such deleterious interactions with non-hydrogen species. In certain embodiments these efforts may be directed to scavenging oxygen and other like species known to those skilled in the art.

By way of specific example, in sensor devices constructed in accordance with the invention, including an yttrium (Y) sensor film 10 overcoated with a Pd film layer 12, the sensor film 10 was found to be sensitive to hydrogen in a nitrogen environment, to hydrogen in a pentane environment, and to hydrogen in an ammonia environment, thus demonstrating the selectivity of the sensing film in such environments.

The integration of such hydrogen-interactive sensor films with micro-hotplate structures in accordance with the present invention permits the selective heating of the sensor film by the micro-hotplate structure, thereby increasing the rate of interaction of the sensor film with any hydrogen gas in the environment being monitored, as well as increasing the rate of regeneration or recovery of the sensor film. Thus, the sensor film may be selectively heated during the active sensing operation so that the reaction of $YH_2 + \frac{1}{2}H_2 \rightarrow YH_3$ is increased, to thereby enhance the sensitivity of the hydrogen sensor device, and after the sensing is complete, the sensor film may be further heated to higher temperature to cause the reverse reaction $YH_3 \rightarrow YH_2 + \frac{1}{2}H_2$ to take place. The micro-hotplate may therefore be coupled with suitable power supply and cycle time controller circuitry, so that the micro-hotplate structure provides appropriate heating of the hydrogen-interactive sensor film for the desired monitoring operation. Such power supply and cycle time controller circuitry may for example be constructed and arranged for pulsed or variable cycle time operation, or according to a selected time-temperature schedule.

Such micro-hotplate structure heating of the hydrogen sensor film significantly enhances the operation of the sensor device of the invention, relative to a corresponding sensor device lacking the micro-hotplate structure. For example, in a sensor device lacking the micro-hotplate structure, for ambient temperature sensing of hydrogen gas, typical response times were on the order of 1 minute after exposure to $H_2$, but complete recovery after removal of the $H_2$ source from the sensor was on the order of hours. By contrast, heating of the sensor film by the micro-hotplate structure substantially improves both the response and recovery times of the sensor device. The micro-hotplate allows electrical measurement of the sensor film while controlling the temperature of the film, thus allowing the formation of the hydride in a highly effective manner.

The hydrogen-interactive sensor film may be readily formed on the micro-hotplate by any suitable deposition techniques, such as, for example, sputter deposition, solution deposition, metal-organic chemical vapor deposition (MOCVD), physical vapor deposition (PVD), and corresponding assisted vapor deposition processes, such as plasma-assisted MOCVD.

The technique for forming the hydrogen-interactive sensor film on the micro-hotplate structure is by physical vapor deposition or chemical vapor deposition. If CVD is employed, then the individual micro-hotplates can be separately heated, in a self-lithographic process flow.

The sensors of the present invention couple novel thin films as the active layer with a MEMS structure known as a Micro-Hotplate. This coupling results in a H$_2$ gas sensor with several unique advantages in terms of speed, sensitivity, stability and amenability to large-scale manufacture. Some embodiments of the present invention have demonstrated response speeds of <0.5 s to 1% H$_2$ in dry air, and the ability to detect <200 ppm. Additionally, the system and method of the present invention can be readily and inexpensively produced at large quantities.

The micro-hotplate structure of the sensor device of the invention may be readily fabricated by micro-machining techniques, as for example based on complementary metal oxide semiconductor (CMOS) fabrication techniques.

One illustrative embodiment of sensor fabrication involves the following steps. A desired micro-hotplate array is designed and laid out, and may for example comprise 4, 8 or more individual micro-hotplate elements. This micro-hotplate array can then be fabricated in a commercial CMOS process using a facility such as the MOSIS system. The resulting micro-hotplate array is micro-machined and packaged. Next, the packaged chip can be placed in either a PVD or a CVD chamber and at least one thin metallic film of the hydrogen-interactive film material can be deposited on the hotplate elements of the micro-hotplate structure. With the appropriate electrical feed-throughs, the hotplate elements can be heated to improve the properties of the metal film deposition. Additionally, with appropriate electrical feed-throughs, the resistance of the deposited films can be monitored in situ and used as a feedback variable for the deposition process. For example, when a specific value of conductance is reached, the film will have a particular thickness, and the conductance value can be utilized for control purposes in the film formation step, to stop the film growth operation at the point that the deposited film reaches the desired thickness. This feedback deposition technique can be used for each of the hydrogen-interactive film and the optional protective over layer film of hydrogen-permeable, extraneous species-impermeable material, to achieve a desired film thickness of each such layer of the sensor element.

Another embodiment would follow the same basic steps as described above, but with the thin metallic film of the hydrogen-interactive film material deposited on the hotplate elements of the micro-hotplate structure before micro-machining and packaging Another embodiment would follow the same basic steps as described above with the exception that an alternative process might be used to fabricate the micro-hotplate structure instead of the CMOS process. Such alternative process might substitute Pt or W for the Al metallization typically used in the CMOS process. In any of such embodiments, both the hydrogen-interactive film and the optional protective-over layer film may be made of different thicknesses within the same array (over different ones of the multiple micro-hotplate elements) to cover a broader dynamic range of hydrogen detection capability. For example, a thinner protective- over layer film of Pd on the hydrogen-interactive sensor film can be used to detect a lower concentration of hydrogen, while a thicker protective-over layer film of Pd on the hydrogen-interactive sensor film can be used to detect a higher hydrogen concentration, since a higher concentration driving force is required for the diffusion of hydrogen through the thicker protective-over layer film to occur, relative to the diffusion of hydrogen gas through a thinner protective-over layer film.

The optimal operation temperature or temperatures of the hydrogen sensors of the invention may be readily empirically determined without undue experimentation, for specific sensing applications.

As a consequence of the rapid thermal rise and thermal fall times that are characteristic of temperatures for micro-hotplate operation, pulsed temperature operation can be advantageously employed in use of the hydrogen sensor device of the invention. For example, as alluded to hereinabove, the hydrogen interactive sensor films may be most sensitive to initial hydrogen exposure at one specific temperature, but require a higher temperature to be returned to their initial state (for subsequent active sensing operation). In such instance, it may be desirable to pulse the micro-hotplate periodically to refresh the hydrogen-interactive sensor film, thereby minimizing the effect of drift and improving long term stability of the device.

The present invention thus makes use of the fact that upon exposure to hydrogen, hydrogen-interactive thin films exhibit striking changes in physical properties, changing from metallic (conducting) to semiconducting phases. These phase changes are accompanied by changes in electrical resistivity, magneto-resistance and photoconductivity of the hydrogenated rare earth thin film.

The invention contemplates a wide variety of sensor devices and apparatus, as well as methodology, which utilize hydrogen-interactive thin films with which hydrogen is interactive to produce both a physical and chemical change in the properties of the hydrogen-interactive thin film.

In the practice of the invention, as described briefly hereinabove, the hydrogen-interactive thin film is overlaid by a protective-over layer which is hydrogen-permeable, but which is at least highly impermeable to reactive species that could otherwise deleteriously interact with the rare earth metal thin film and prevent it from producing the desired physical property change of the film incident to exposure of the film to hydrogen. These alloys may suppress this phase transition in rare earth films such as palladium by alloying with suitable elements, such as silver, titanium, nickel, chromium, aluminum or other species known to those skilled in the art. In this manner, the long-term stability of the underlying coating can be improved. Reducing percentage Ag alloying to 10% slowed the recovery rate. Reducing the coating thickness and percent Ag alloying are methods to improve the recovery rate of the Ag alloyed Pd films. Reducing the total capping film thickness to about 15 nm (12 nm Pd and 3 nm Ag) improved the sensor's reaction and recovery rates. While reducing the Ag to 10% significantly degraded the sensor's performance The palladium thin film may need more than 10% Ag alloy to be fully stabilized.

The gradual oxidation of the rare earth sensing film 10 is responsible for long term signal shift, and this oxidation is exacerbated by repeated cycling of the palladium from the α to β hydride phases. Consequently, the present invention focuses on the optimization of the noble metal capping layer 12 through alloying, as this phase change in palladium can be suppressed by alloying with silver, chromium, nickel, titanium or other like metals as known to those skilled in the art. Several experimental factors as listed in Table 1 may be altered to investigate a number of compositions and their effect of sensor stability.

| Factors effecting sensor stability |
|---|
| Active Layer Primary Element |
| Active Layer Dep. Temp. |
| Active Layer Thickness |
| Active Layer Deposition Rate |

-continued

Factors effecting sensor
stability

Capping Layer Primary Element
Capping Layer Deposition
Temperature
Capping Layer Dopant/Alloy
Capping Layer Deposition Rate
% Alloy
Total barrier layer thickness
Number of layers As used herein, the term "hydrogen-interactive thin film element" means one or more thin films wherein at least one thin film is selected from the group consisting of one or more rare earth metals, one or more Group II elements as well as alloys or combinations thereof. As used herein the term "rare earth metal means a metal selected from scandium, yttrium, lanthanum, the lanthanides, and the actinides as well as alloys and combinations of such metals, and alloys and combinations of such metals with Group II elements, e.g., calcium, barium, strontium, magnesium and radium. The lanthanides are the 14 elements following lanthanum in the Periodic Table, viz., cerium, praseodymium, neodymium, promethium, samarium, europium, gadolinium, terbium, dysprosium, holmium, erbium, thulium, ytterbium and lutetium. The actinides are the elements of the Periodic Table having the atomic numbers 89 through 103 inclusive, viz., actinium, thorium, protactinium, uranium, neptunium, plutonium, americium, curium, berkelium, californium, einsteinium, fermium, mendelevium, nobelium and lawrencium.

The physical property of the hydrogen-interactive thin film that is altered in response to the presence of hydrogen may be the optical transmissivity of the film to optical radiation incident on the sensor element, electrical resistivity, electrical conductivity, magneto resistance, photoconductivity, electrical capacitance, or any other physical and/or chemical properties that are changed in exposure of the hydrogen-interactive thin film to hydrogen. Appropriate detector and output components, to provide an output indicative of the presence of hydrogen in the environment to which the hydrogen-interactive thin film of the sensor is exposed, readily monitor the change in physical property of the hydrogen-interactive thin film.

The aforementioned changes in properties of hydrogen-interactive thin films, incident to their exposure to hydrogen, result from a chemical equilibrium between the dihydride and trihydride forms of such films. When hydrogen is present, a dynamic equilibrium exists between the two forms and the physical and optical changes can be quite dramatic.

For example, in the presence of hydrogen, noble metal (e.g., Pd, Pt) overcoated Y reacts to form the dihydride ($YH_2$). Further exposure to hydrogen results in the formation of the trihydride $YH_3$. This second step occurs at room temperature (e.g., about 25 degrees Centigrade) and ambient pressure (e.g., about 1 atmosphere) and is completely reversible. The formation of $YH_2$, on the other hand, is essentially irreversible at room temperature and ambient pressure, as a result of its relatively large heat of formation (−114 kJ/mol H) compared with the equilibrium step (−41.8 kJ/mol H or −44.9 kJ/mol H). This process is illustrated in the following formula:

$$Y + H_2 \rightarrow YH_2 \xrightarrow{1/2\, H_2} YH_3$$

The transition of the optically reflecting rare earth dihydride to the optically transparent rare earth trihydride is a chemical change with electronic origins. The dark blue reflecting phase of $YH_2$ is metallic, whereas the transparent phase ($YH_3$) is semiconducting with a direct band gap of 1.8 eV. This change of state—from metallic to semiconducting—can therefore be readily quantified by measuring the resistance of the film under hydrogen exposure conditions. Resistance measurements allow the correlation of the optical and electrical behavior of the films.

As a consequence of the ability of micro-hotplates to localize high temperature heating to microscopic regions of the device structure, the sensors of the present invention can utilize elevated temperatures to enhance the hydrogen sensing operation without the dangers of hydrogen ignition that have plagued the prior art "hot wire" sensors described in the Background section hereof.

Further, the temperature control capability of the micro-hotplate structure permits the thermal management of the sensor in a highly effective and efficient manner. Qualitatively the rare earth dihydride to trihydride transition is an exothermic chemical reaction (negative ΔG: −41.8 kJ/mol H or −44.9 kJ/mol H). Thus, the micro-hotplate structure can be selectively actuated and controlled to provide appropriate temperatures favorable to hydrogen gas sensing.

While we do not wish to be bound by any theory as regards the specific mode or mechanism of behavior of the rare earth thin film sensors in accordance with the present invention, it is believed that a metal-insulator transition rather than a structural phase change causes the observed physical properties transformation.

The selectivity exhibited by hydrogen-interactive thin films allows, for the first time, fabrication of inexpensive hydrogen sensors that can be deployed in large numbers to remotely monitor hydrogen levels over large areas. Furthermore, hydrogen-interactive thin films can operate in an industrial or manufacturing environment containing trace organic vapors. We are not aware of any existing hydrogen sensing technologies having these attributes.

Hydrogen-interactive thin films can be coated with materials such as palladium or platinum to provide an effective barrier to oxidation, yet enable hydrogen to diffuse through to the rare earth thin film, thereby acting as a selective membrane for hydrogen in the sensor element.

The deposition of hydrogen-interactive thin films on the micro-hotplate substrate may be readily carried out using at least one organometallic precursor of the rare earth metal or the Group II element that thermally decomposes to the metal hydride or elemental metal in a reducing environment of hydrogen. Under some conditions, the direct formation of rare earth metal hydride materials may be realized.

The invention enables a hydrogen detection system to be constructed for monitoring an extended or remote area region for the incursion or generation of hydrogen therein. The hydrogen detection system may include a multiplicity of rare earth metal thin film/micro-hotplate detector devices each of which (i) is arranged for exposure to a specific individual locus of the extended area region and (ii) exhibits a detectable change of physical property, e.g., optical transmissivity, electrical resistivity, electrical conductivity, electrical capacitance, magneto-resistance and/or photoconductivity, when the hydrogen-interactive thin film of the detector device is contacted with hydrogen gas at such locus.

The hydrogen detection system described in the preceding paragraph may be constructed and arranged so that different physical properties are detected when multiple detector devices are contacted with hydrogen gas at different loci of the extended area region.

The hydrogen sensor of the invention is readily fabricated by forming on the micro-hotplate substrate a hydrogen-interactive thin film that is responsive to contact with hydrogen by exhibiting a detectable change of physical property, and coupling the thin film with means for exhibiting the detectable change of physical property when the hydrogen-interactive thin film is exposed to hydrogen.

The means for exhibiting the detectable change of physical property when the hydrogen-interactive thin film is contacted with hydrogen gas, may for example comprise a colored substrate, whereby the detectable change of physical property entails a change from opacity to transparency when the hydrogen-interactive film is contacted with hydrogen gas or a change in color as determined by the colored layer in close proximity to the hydrogen sensitive layer (lanthanum hydride film) in its transmissive form. By such arrangement, the colored substrate is obscured in the absence of hydrogen, and rendered visible when hydrogen is present and converts the formerly opaque film to a transparent film.

The means for exhibiting the detectable change of physical property when the hydrogen-interactive thin film is contacted with hydrogen gas may include suitable circuit means for signal processing the change of physical property and generating an output indicative of the presence or absence of hydrogen gas.

In the practice of the invention, the hydrogen-interactive thin film is formed on the substrate by a technique such as physical vapor deposition, chemical vapor deposition, sputtering, solution deposition, focused ion beam deposition, electrolytic plating, or electroless plating. The hydrogen-interactive thin film may also be separately both metal dihydride and metal trihydride reaction products, wherein the metal dihydride and metal trihydride reaction products have differing physical properties. The physical property change may for example include an optical transmissivity change, such as a change of optical opacity to optical transparency and discretely formed as an independent element, remotely from the micro-hotplate structure, and subsequently secured or placed on the micro-hotplate structure, to form the integrated sensor.

Most preferably, the hydrogen-interactive thin film is formed on the substrate by physical vapor deposition, or alternatively by chemical vapor deposition, e.g., by liquid delivery chemical vapor deposition, using an organometallic precursor that thermally decomposes to the metal hydride or elemental metal in a reducing environment of hydrogen.

The hydrogen-interactive thin film in the sensor may in one embodiment comprise a rare earth metal thin-film. The rare earth metal thin film may include a rare earth metal component such as a trivalent rare earth metal, e.g., yttrium or lanthanum, that is reactive with hydrogen to form when the rare earth metal thin film is contacted with hydrogen gas. The physical property change may comprise a change from a metallic state to a semiconducting state, whereby the step of monitoring the physical property to determine the presence of hydrogen gas in the environment may be carried out by monitoring the electrical resistance, conductance, capacitance, or other electrical property of the rare earth metal thin film.

The rare earth metal thin film in the broad practice of the invention may suitably comprise at least one metal selected from the group consisting of: scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, and lawrencium, alloys thereof, and alloys containing one or more of such metals alloyed or doped with a suitable dopant component such as copper, cobalt, iridium, magnesium, calcium, barium, strontium,etc.

The hydrogen-permeable material of the protective hydrogen-permeable barrier layer may suitably comprise a metal such as Pd, Pt, Ir, Ag, Au, Co, Al and/or alloys thereof.

As a further variation, the hydrogen-permeable protective over layer may be formed of alternating material layers. The material layers may be formed of Pd, Ir and/or Pt.

As used herein, the term "thin films" will be understood as broadly referring to films having a thickness of less than about 1,000 microns.

In the use of hydrogen-interactive thin films in the practice of the invention for hydrogen sensing applications in which the thin film will or may encounter oxidizing species in the environment being monitored for hydrogen, such as oxygen, moisture (relative humidity), nitrogen oxides, carbon oxides, etc., it is advantageous to coat or encapsulate the hydrogen-interactive thin film with a hydrogen-permeable protective material that prevents such oxidizing species, as well as other deleterious species in the environment, from contacting the hydrogen-interactive thin film.

The protective material may for example absorb oxygen and allow diffusion of hydrogen through the protective material to the rare earth metal thin film. Alternatively, the protective material may be impermeable to oxygen and/or other oxidizing species.

The protective material when present as an over layer coating or encapsulant should be continuous and atomically dense in order to provide an effective barrier against oxidation. The thickness of the over layer may be readily selected to minimize oxygen permeation while maximizing the response of the hydrogen-interactive thin film to hydrogen.

In one embodiment of the present invention in which a protective material over layer is employed, the over layer may be formed of a metal such as Pd, Pt, Ir, or alloys or combinations thereof with one another or with other metal species. Particularly useful alloys for such protective material over layers include Pd—Ag (20%).

The CVD process when used to form the hydrogen-interactive thin film on the substrate, may employ bubbler delivery or liquid delivery with subsequent flash vaporization, using a suitable precursor or source compound, to generate a precursor vapor, which is transported to the heated micro-hotplate substrate for decomposition to form the desired hydrogen-interactive film. Such precursors must be robust and volatile at the temperature of vaporization, yet they must decompose cleanly and efficiently on the substrate.

Particularly precursors for rare earth metal thin film formation by CVD in the practice of the invention include tris(cyclopentadienyl)lanthanum, tris(cyclopentadienyl) yttrium, β-ketoamine complexes of lanthanum, β-ketoamine complexes of yttrium, β-diiminate complexes of lanthanum, β-diiminate complexes of yttrium; lanthanum amides, and yttrium amides.

Suitable precursors may be readily determined within the skill of the art by screening techniques conventionally used in the art of CVD formation of thin films, including thermo gravimetric analysis (TGA) and differential scanning calorimetry (DSC) analysis.

For example, such simultaneous thermal analysis (STA) studies under argon and vacuum may be conducted to screen candidate precursors for suitable thermal stability and transport properties.

The STA studies are suitably conducted under conditions simulating CVD conditions, e.g., under a flow of $H_2$ (5%) diluted with argon to provide data for predicting the major decomposition pathway(s) of the candidate precursors.

This combination of tests allows for rapid screening of a number of potential precursors, and also allows the study of the effect of other species present in the CVD process, e.g., reducing agents such as $NH_3$, on the decomposition pathway.

For example, hydrogen-interactive material thin films are from about 50 to about 2000 nm thick, more preferably from about 50 to about 200 nm thick, with a protective layer when present having a thickness of from about 2 to about 1000 nm, and more preferably from about 2 to about 100 nm, e.g., a 20 nm thick protective layer of a material such as Pd on a rare earth metal thin film of 100 nm thickness. The protective over layer is preferably thick enough to adequately protect the sensor from oxidation and thin enough to leave unchanged the properties being monitored in the operation of the device.

The protective over layer may be deposited or formed over the hydrogen-interactive thin film in any suitable manner, including spraying, solution deposition, dipping, chemical vapor deposition, physical vapor deposition, focused ion beam deposition, sputtering, etc. Generally, the methods described hereinabove for formation or coating of the hydrogen-interactive thin film in the first instance may also be used for forming the protective over layer thereon, and vice versa.

The protective over layer may be formed of any suitable material of construction, which is suitably effective to prevent chemical reaction or sorption processes from occurring that would preclude the efficacy of the hydrogen-interactive thin film for hydrogen sensing.

Although the protective over layer material is typically in the form of a film that is formed directly on the underlying hydrogen-interactive thin film, it is possible within the broad scope of the present invention to utilize a protective material such as a free-standing film or a membrane that is in spaced relationship to the hydrogen-interactive thin film.

For example, the protective material may comprise a membrane that is permselective for hydrogen only. The membrane may thus form a cell within which the hydrogen-interactive thin film is deployed.

The protective over layer material may for example be a metal, a polymeric film material, a vitreous or ceramic material, etc. Examples of useful metals include Pd and other noble metals such as Pt, Ir, etc.

In the practice of the invention, Pd is utilized as a protective over layer material, and may be usefully deposited on the hydrogen-interactive thin film by chemical vapor deposition from a corresponding precursor.

Examples of precursors that may be used as source compositions for deposition of Pd by CVD include Pd(hfac)$_2$, Pd(allyl)$_2$ and CpPd(allyl).

In an aspect of the invention, the thickness of a Pd or other noble metal protective over layer is selected to optimize the response of the films to hydrogen. The over-layer is desirably continuous and atomically dense in order to provide an effective barrier against oxygen. The thickness of the protective layer is strongly dependent on the average roughness of the underlying film. The smoother the topography of the underlying hydrogen-interactive, the thinner the protective over layer can be to provide effective coverage.

Pd absorbs approximately nine hundred times its volume of hydrogen gas. Although such absorption is reversible and highly selective for hydrogen, excessive dissolution of hydrogen in the Pd protective over layer may slow its diffusion to the underlying hydrogen-interactive thin film. Such hydrogen dissolution may also result in slow "re-zeroing" of the sensor after detection of hydrogen, due to slow rates of desorption, and the thermal actuation and output of the micro-hotplate are desirably utilized to compensate for the system "restoration delay" that would otherwise result in the absence of thermal recovery operation by the micro-hotplate structure.

Both Pt and Ir absorb hydrogen and allow hydrogen to diffuse through them and can readily be used in place of Pd. A number of Pd-rich alloys also absorb hydrogen, e.g., Pd—Ag (20%). Membranes of this alloy do not undergo the volume expansion and cracking that is sometimes observed for pure Pd and that may limit the use of such pure material. Pd-rich alloy membranes are used industrially and may be advantageously employed in the broad practice of the present invention.

Rare earth metal alloys of magnesium are also useful as the hydrogen-interactive sense layer. The overall optical transmission rate of a rare earth-magnesium alloy hydride is higher than that of the pure metal hydride. The heat of formation of magnesium hydride (−33 kJ/mol H) is similar to that of rare earth hydrides (c.a. ~40 kJ/mol H) and the uptake of hydrogen by these alloys is reversible. In addition, the band gap of magnesium hydride is large enough that it forms a transparent hydride.

Alloying Gd with Mg to form the hydrogen-interactive sensing layer yields a number of benefits. The alloyed films display much higher transmittance than pure Gd films. In Gd—Mg (30%) alloys maximum transmittance is achieved at pressures well below 0.1 bar. This characteristic makes the alloyed film very sensitive to hydrogen. The slope of total transmittance vs. P[$H_2$] curve, below 1 bar, changes considerably with the concentration of Mg in the film. Alloying with a suitable metal, therefore, permits the sensory response of the film to be selectively "engineered" for specific concentrations of hydrogen in the product sensor device.

Alloying also increases the transmission ratio (i.e., transmission of hydrided film/transmission of dehydrogenated film) to over 3000. This is due to the virtual elimination of all residual transmission in the visible window. Residual transmission is typically small (c.a. 1.5%) and of indeterminate origin. It is observed when samples exposed to hydrogen are allowed to desorb in air. Alloying with magnesium shifts the transmission window to shorter wavelengths while gradually reducing the % transmission. For Gd—Mg alloy films containing 30 at. % Mg, the maximum transmission of a 200 nm layer is 0.01%. These properties make the Gd—Mg composition useful as an active layer material to form a highly sensitive thin film sensor.

Alloys containing Mg at concentrations higher than 50 at. % exhibit three different optical states: transparent, absorbing, and reflecting; rather than just transparent and reflecting. This observation can be exploited to provide another intermediate sensory response, and enables the use of such alloys in tri-state optical switches.

The foregoing examples illustrate the utility of engineering the band gap and free energy of the rare earth dihydride to trihydride transition, and such modification may be effected in the broad practice of the invention by the addition to the hydrogen-interactive thin film of a wide variety of potentially suitable dopants.

The specific dopant employed, and its concentration, are appropriately selected to enable the formation of an alloy hydride that has a band gap large enough to be transparent in the visible region or otherwise appropriately constituted for a detectable change of property or properties in exposure to hydrogen. Ideally, the dopant will also render the dihydride to trihydride equilibrium thermodynamically neutral. Mg, Ca, Ba, Sr, Al, Ir and Co is potentially useful dopant species for such purpose. Transition metal elements such as Co and Ir form a variety of stoichiometric and non-stoichiometric hydride species and may be particularly useful in a given end use application.

In one embodiment of the invention, the hydrogen-interactive thin film may be layered comprising one or more thin films wherein at least one thin film is selected from the group consisting of rare earth metals, Group II elements or any combination thereof. The rare earth metal and the Group II element may be combined to form a Group II element doped rare earth metal thin film or an alloy thin film comprising the rare earth metal and the Group II element. This embodiment represents another technique for selectively varying the response characteristics of the hydrogen-selective thin film to achieve a desired sensory sensitivity for the hydrogen-selective thin film sensor.

Doping techniques are well known by those skilled in the art. Doping may include the addition of at least one element impurity to the hydrogen-interactive thin film or the deposition of a thin film adjacent to the hydrogen-interactive thin film so as to produce a hydrogen-interactive thin film with a desired characteristic.

In another embodiment of the invention, the protective over layer on the hydrogen-interactive thin film may be layered, with alternating constituent layers of over layer materials such as Pd, Ir, Rh, Ag, Au, Co, Pt and/or alloys thereof, as another technique for selectively varying the response characteristics of the protective over layer to achieve a desired sensory sensitivity for the hydrogen-selective thin film sensor.

For example, a sensory Y and/or Gd film may be formed with alternating protective over layers of elements such as Pd and Pt, to provide maximum sensitivity and capability over a wide range of hydrogen concentration. The Pd/Pt interlayer in such a structure acts as hydrogen storage layers as well as oxygen barrier layers, thereby enhancing the sensitivity of the film. Such a construction also allows reduction of the thickness of the top layer well below 50 Å.

In another embodiment of the invention, the hydrogen-interactive thin film sensor may comprise a multi-layered hydrogen-interactive element wherein, a first deposited thin film comprising Mg is deposited adjacent to the micro hotplate structure and a second thin film comprising Y is deposited adjacent to the first deposited Mg thin film wherein, the multilayered hydrogen interactive element comprising a first Mg thin film and a second Y thin film would be coated with a Pd protective over layer.

In an embodiment of the invention, the hydrogen-interactive thin film sensor may comprise a hydrogen-interactive element wherein, a thin film of Y is deposited adjacent to the micro hotplate structure, and a Pd protective over layer is deposited adjacent to the hydrogen interactive element.

In another embodiment of the invention, the hydrogen-interactive thin film sensor may comprise a hydrogen-interactive element wherein, a thin film consisting of 30 At % Mg and 70 At % Y is deposited adjacent to the micro hotplate structure, and a Pd protective over layer is deposited adjacent to the hydrogen-interactive element.

The foregoing illustrative materials, Pd, Ir, Rh, Ag, Au, Co, Pt and/or alloys thereof, may be deposited to form the sensor device by any suitable method, with CVD being generally . A wide variety of useful precursors for such CVD formation of the material on a given substrate or intermediate structure of the sensor may be readily determined within the skill of the art and without undue experimentation.

Examples of potentially useful precursors for Mg and Ir include $Mg(thd)_2$ and $(COD)Ir(hfac)$, respectively.

Precursors for Al include, for example, the dimethylethyl amine adduct of alane ($AlH_3$) or dimethylaluminumhydride (DMAH), an air sensitive volatile liquid that is useful to deposit high quality aluminum films.

Cobalt precursors include cobalt beta-diketonates such as $Co(thd)_2$ or $Co(hfac)_2$.

Figure 4:
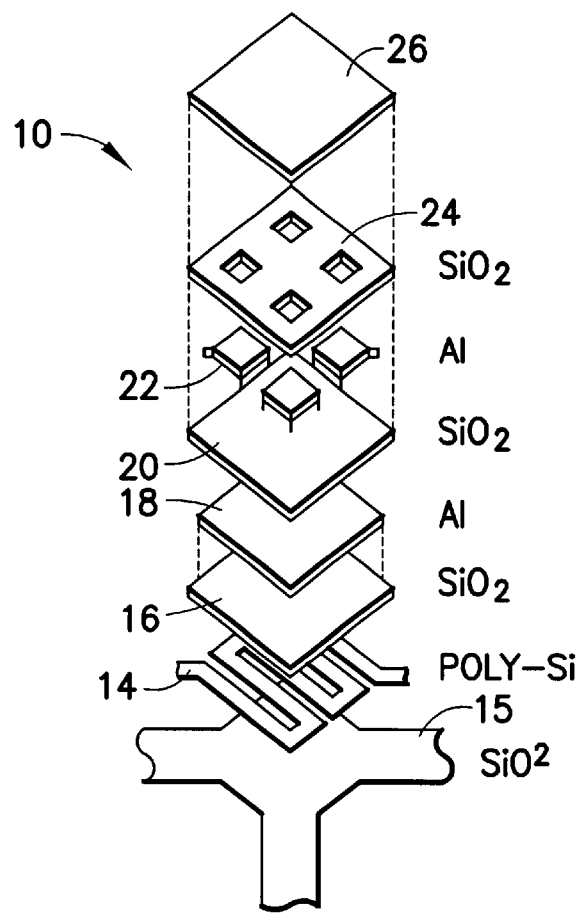
FIG. 4 is an exploded view of constituent layers of a hydrogen sensor according to one embodiment of the present invention.

Referring now to the drawings, FIG. 4 is a scanning electron microscope (SEM) micrograph of a thin film sensor including a thin film sensor element deposited by metal organic chemical vapor deposition (MOCVD) on a micro-hotplate structure. The micro-machined sensor platforms define a 4-element gas-sensing array in which the active elements are shown as light gray regions.

Figure 5:
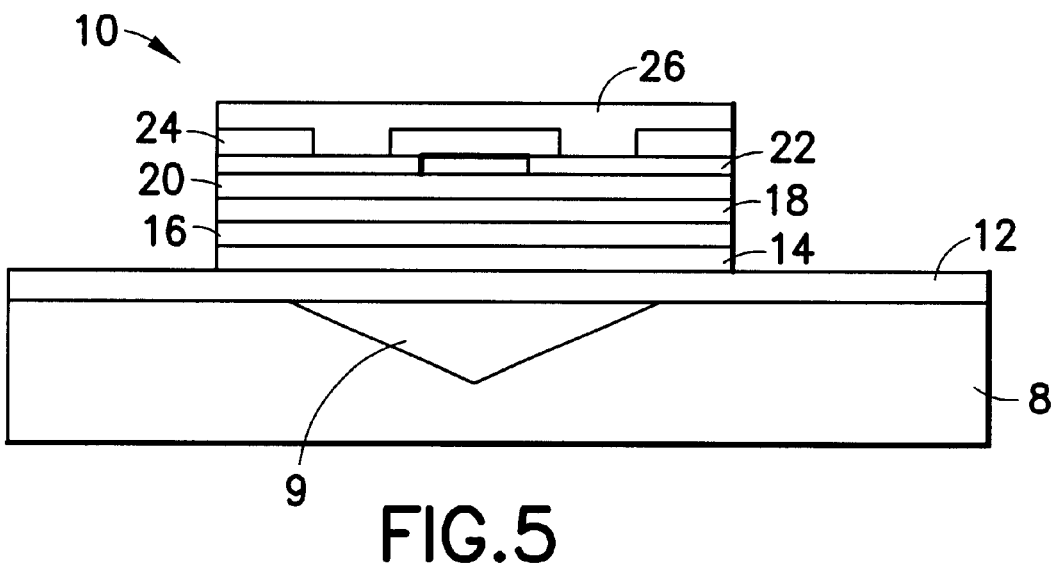
FIG. 5 is a schematic cross-sectional elevation view of a hydrogen sensor according to one embodiment of the present invention showing the constituent layers of the structure on a silicon substrate.

FIG. 5 is an exploded view of constituent layers of a hydrogen sensor 10 of the type shown in FIG. 4, and constructed according to one embodiment of the present invention. The lowermost layer 15 is formed of silicon dioxide ($SiO_2$) and defines a suspended membrane or micro bridge. The next succeeding layers include polycrystalline silicon heating element 16, silicon dioxide insulating layer 17, conductive heat distribution plate 18 formed of aluminum, silicon dioxide insulating layer 20, four aluminum contact pads 22, and silicon dioxide insulating layer 24 with four openings therein communicating respectively with the four aluminum contact pads 22. The layers 15, 16, 17, 18, 20, 22 and 24 corporately constitute the micro-hotplate structure of the hydrogen sensor.

Overlying the silicon dioxide insulating layer 24 is the thin film sensor layer 26. The thin film sensor layer 26 may comprise only a rare earth metal thin film, or such rare earth metal thin film may be optionally overlaid with a hydrogen-permeable protective barrier layer thin film.

The micro-hotplate structure of the hydrogen sensor shown in FIG. 5 may be constructed as more fully described in U.S. Pat. No. 5,356,756 to R. Cavicchi, et al. Typical physical characteristics are listed in Table 1 for the micro-hotplate structure of FIG. 5 comprising the thermally isolated, suspended resistive heater, the thin film thermometer, and the four contact pads for measuring the conductance of the active layer.

TABLE 2

| Typical Micro-hotplate Physical Characteristics | |
|---|---|
| Suspended Mass | ~0.2 □g |
| Suspended Area | 100 □m × 100 □m, |
| Maximum Surface Temperature | 550° C. |
| Thermal rise time, fall time | 1–3 ms, 3–4 ms |
| Continuous-use Power Consumption | 60 mW |

FIG. 5 is a schematic cross-sectional elevation view of a hydrogen sensor 10 according to one embodiment of the present invention showing the constituent layers of the structure on a silicon substrate 8. In the FIG. 5 device, elements corresponding to those of FIG. 4 are correspondingly numbered. In the device structure of FIG. 5, the silicon dioxide layer 15 is overlaid in sequence by polycrystalline silicon heating element layer 16, silicon dioxide insulating layer 17, conductive (Al) heat distribution plate layer 18, silicon dioxide insulating layer 20, Al contact pads 22, silicon dioxide insulating layer 24. The silicon substrate 8 is removed from the pit 9 therein, below the silicon dioxide, thus creating a suspended micro bridge. The suspended structure is overlaid with the thin film sensor layer 26, including a rare earth metal thin film optionally overlaid with a hydrogen-permeable protective barrier layer thin film to prevent oxygen and other oxidizing species from contacting the rare earth metal thin film.

Figure 6:
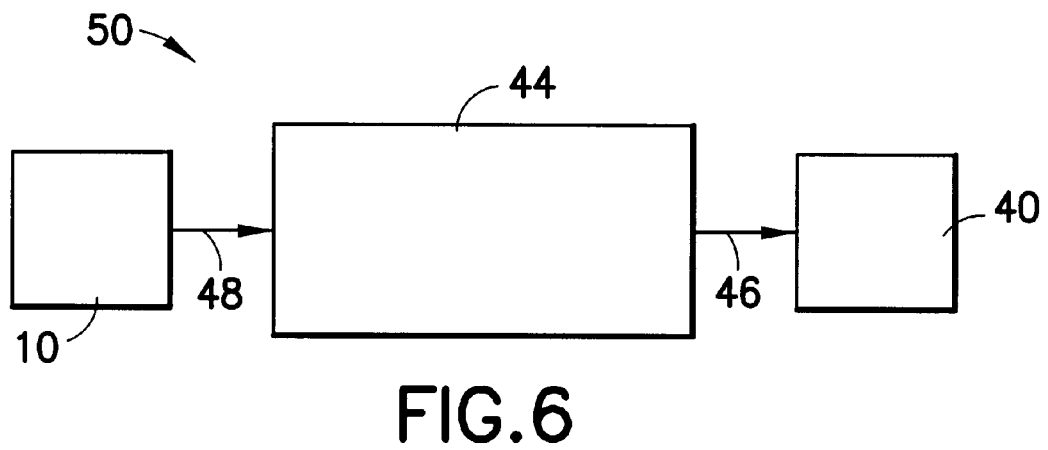
FIG. 6 is a schematic representation of a hydrogen sensor apparatus according to one embodiment of the invention.

FIG. 6 is a schematic representation of a hydrogen sensor apparatus 50 according to one embodiment of the invention. The hydrogen sensor apparatus 50 includes a hydrogen sensor device 10 that may be constructed and arranged as described hereinabove.

The hydrogen sensor device 10 is connected by signal transmission line 48 to the central processor unit 44, which may comprise microprocessor or computer control elements for actuation, monitoring and control of the hydrogen sensor device. The central processor unit 44 processes the signal carried by signal transmission line 48, and produces an output signal that is transmitted in signal transmission line 46 to output device 40, which produces an output that is indicative of the presence or absence of hydrogen in the environment to which the sensor is exposed.

The output of the central processor unit 44 may include any perceivable output, such as auditory output, visual output, tactile output (as for example when the hydrogen sensor apparatus is adapted to be worn on the body of a user, and the central processor unit comprises a vibrator imparting vibratory sensation to the user's body when hydrogen is detected in the environment, such as may be useful in environments where auditory or visual outputs are not readily perceivable.

In lieu of producing an output, which is perceivable, the central processor unit 44 may be programmed to actuate means for eliminating hydrogen from the environment being monitored, as for example a sweep gas flushing operation to purge the environment of the hydrogen gas.

It will be recognized that the hydrogen sensor may be constructed so that the rare earth metal thin film is arranged in hydrogen permeation exposure to the environment being monitored. For example, the active face of the sensor defined by the layer 26 in the FIGS. 5 and 6 drawings may be contained in a sensing head which is insertable into a specific gas environment susceptible to the incursion or in situ generation of hydrogen therein.

The CPU 44 may be programmably arranged to maintain an appropriate monitoring status indicative of the presence or absence of hydrogen gas in the environment being monitored. The CPU may include an electrical resistivity monitor communicating by signal transmission line 48 with the hydrogen sensor device 10, to monitor the change in electrical resistivity of the film element incident to the introduction of hydrogen into contact with the hydrogen sensor device 10, and to responsively generate a corresponding output signal.

Figure 7:
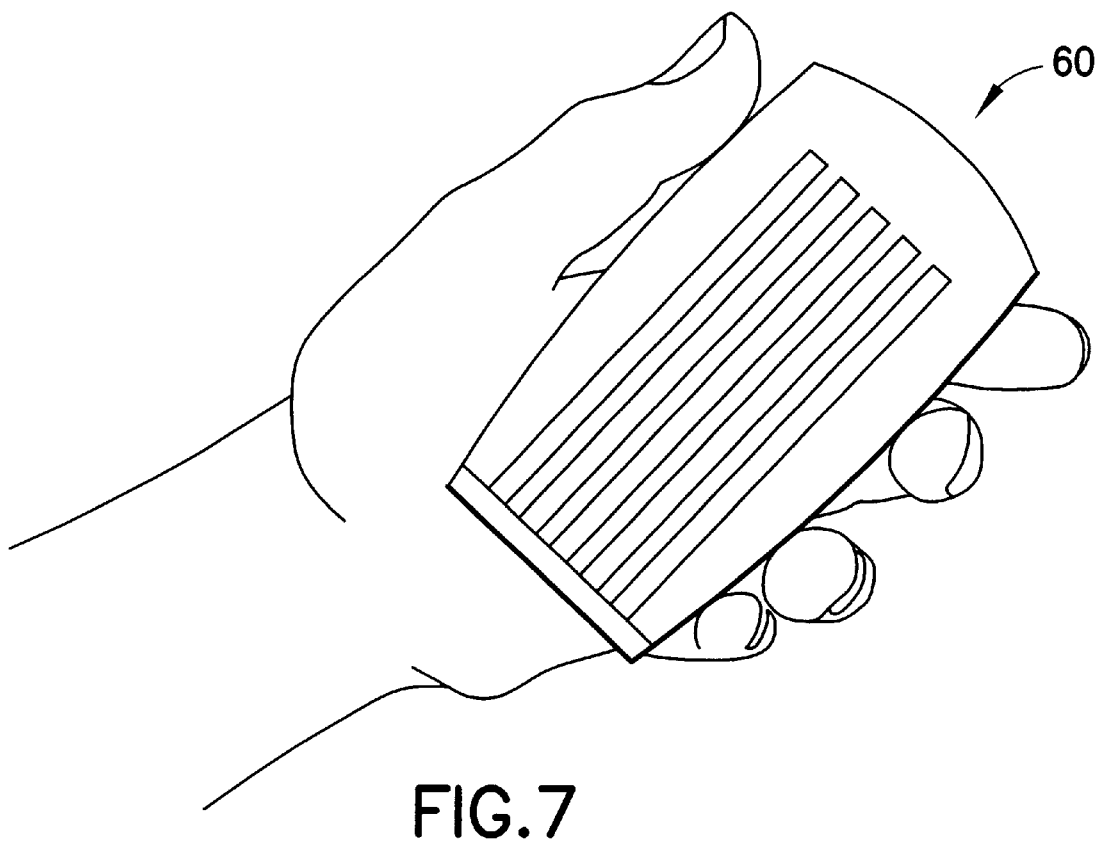
FIG. 7 is a perspective view of a hand-held hydrogen sensor apparatus according to one embodiment of the present invention.

FIG. 7 is a perspective view of a hand-held hydrogen sensor unit 60 according to one embodiment of the present invention, comprising the sensor apparatus in housing adapted for manual transport and deployment. The sensor unit 60 may for example be constructed with an audible alarm indicating the presence of hydrogen gas in the environment being monitored. Such hydrogen sensor unit may be conveniently fabricated as a solid-state battery-powered device, with a very small weight.

It will be appreciated that the hydrogen sensor of the present invention may thus be provided in a wide variety of potentially useful configurations, for a corresponding variety of hydrogen sensing applications.

Figure 8:
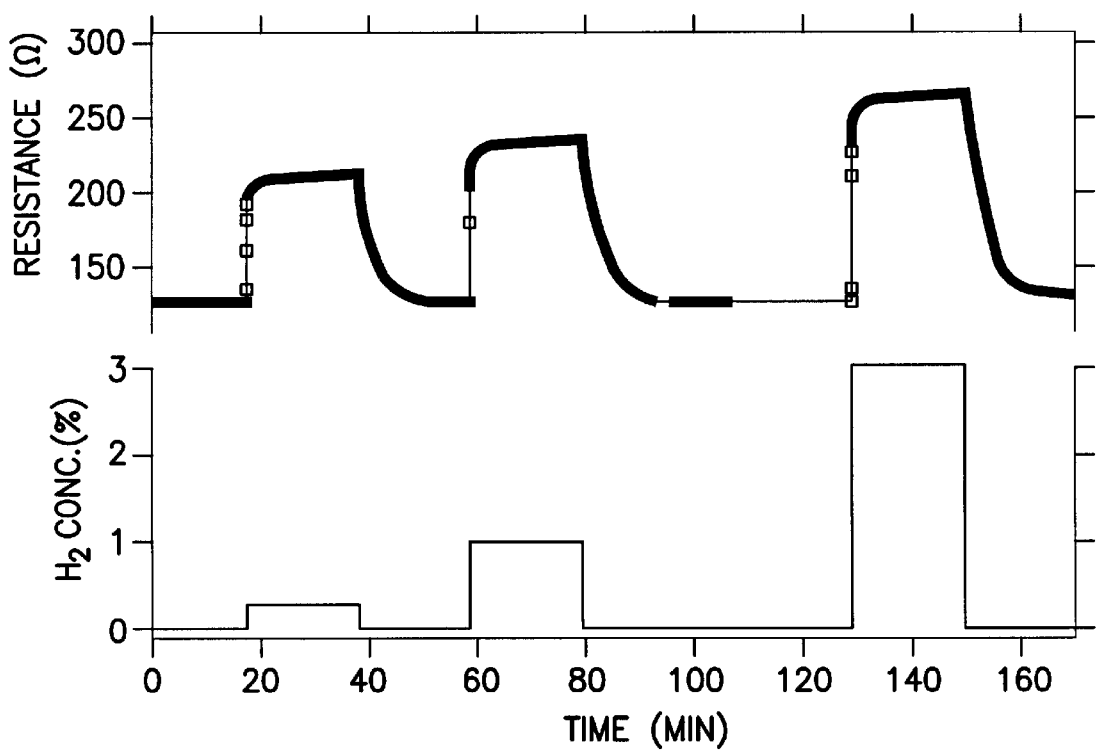
FIG. 8 is a graph showing the resistance response of a palladium/yttrium micro-hotplate sensor as a function of time when exposed to various concentrations of hydrogen in a background gas of 1 atmosphere of nitrogen.

FIG. 8 is graph of the response of a $H_2$ sensor including a 15 nm thickness of palladium deposited on 300 nm of yttrium, overlaid on a suspended micro hotplate structure. The top panel of the graph shows the measured resistance of the sensing film as a function of time, and the bottom panel of the graph shows how the concentration of $H_2$ was varied with time. The testing was done at atmospheric pressure, in a nitrogen ambient environment. The micro hotplate element was held at a temperature of ~400° C. There is rapid increase in resistance when $H_2$ is introduced to the sensor, and magnitude of the response increases with increasing $H_2$ concentration.

Figure 9:
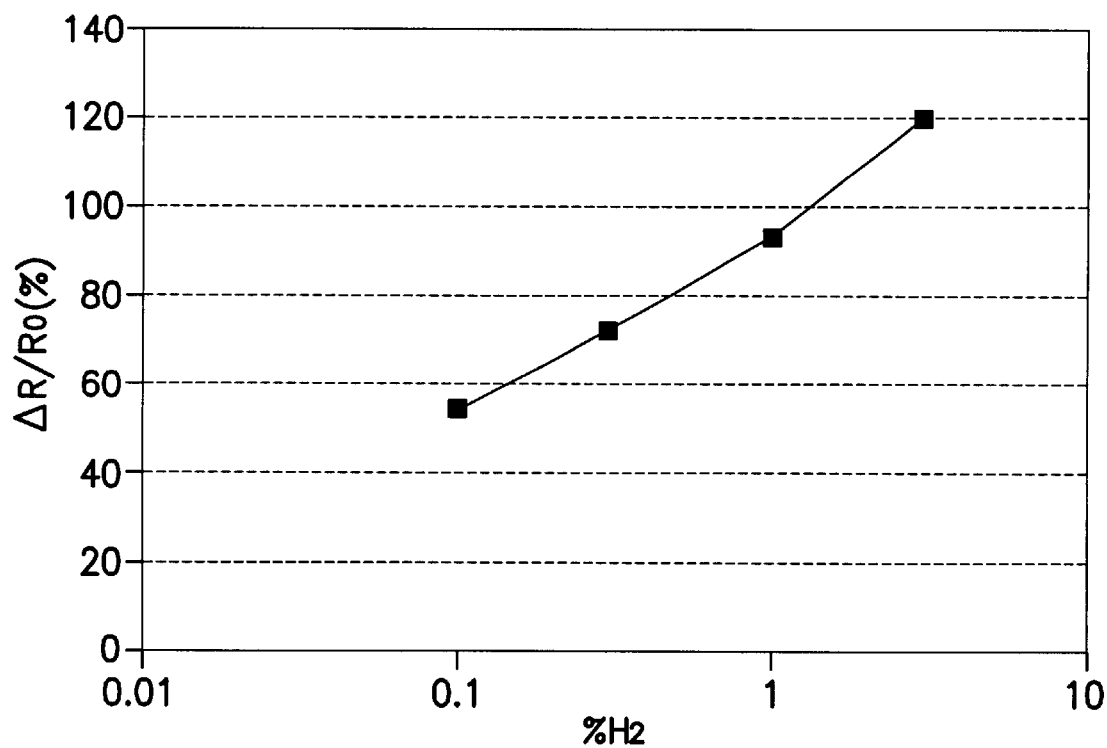
FIG. 9 is a graph showing the resistance response of a palladium/yttrium micro-hotplate sensor as a function of hydrogen concentration, for hydrogen exposures carried out in a background gas of 1 atmosphere of nitrogen.

FIG. 9 is graph of the response of a $H_2$ sensor including a 15 nm layer of palladium deposited on 300 nm of yttrium, overlaid on a suspended micro hotplate structure, as a function on $H_2$ concentration. The testing was done at atmospheric pressure, in a nitrogen ambient and the micro hotplate element was held at a temperature of ~400° C. The response of the sensor is approximately linear with respect to the log of the $H_2$ concentration over the range tested, viz., 0.1% to 4% $H_2$. The character of such response suggests that such range could readily be extended from 0.01 to 10% of the range that was tested, which is a dynamic range of 3 orders of magnitude.

The measured response of these gas sensors is the change in resistance that occurs in the active layer film stack when exposed to hydrogen, where the resistance of the film increases with increasing hydrogen concentration. Based on the design flexibility of the micro-hotplate, the resistance of these films can be measured in either a 2-wire or a 4-wire configuration.

Accurately measuring the speed of response to $H_2$ of the gas sensors is an important design consideration for both the data collection systems and the gas handling manifolds utilizing these sensors. One embodiment of the present invention uses an automated system for the data collection based on an HP 34970A DMM data logger with an HP 34902A scanning card. This system is capable of a scanning speed of 250 channels/s. In order to achieve fast gas switching speeds, the gas handling manifold used low volume gas chromatography valves in combination with ⅛" tubing and a small test chamber size. However, one should note that the present invention need not be limited to this specific embodiment or configuration.

The ambient gas used for the experiment was triple filtered compressed air that was passed through a membrane drier, with a dewpoint specification of −40° C. Grade 5.0 hydrogen was used and blended with the air using mass flow controllers with ranges of 200 and 5000 sccm respectively.

Figure 10:
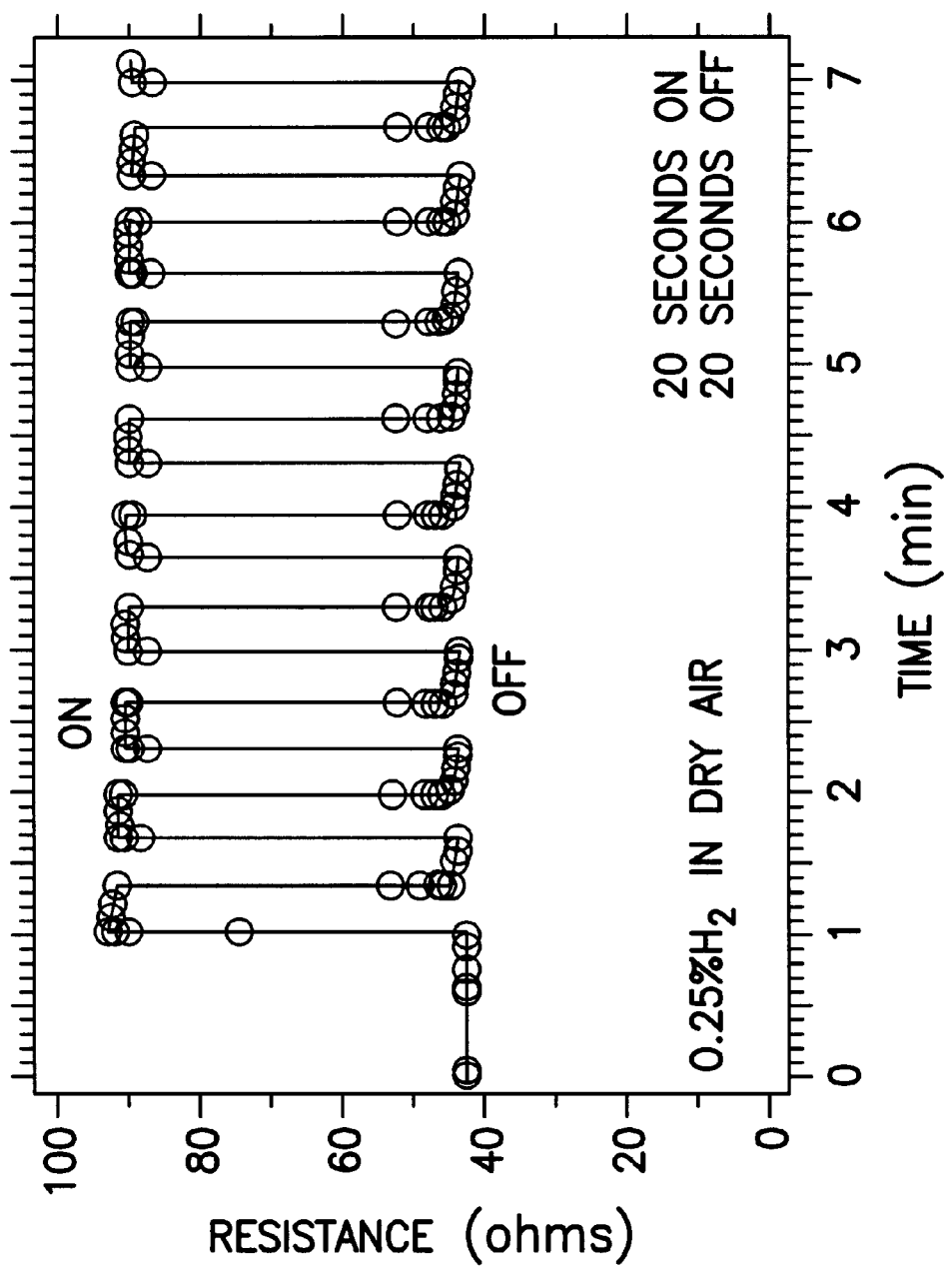
FIG. 10 plots the Resistive response of a micro hotplate based $H_2$ gas sensor to repeated exposure to 0.25% $H_2$ in air. The magnitude of response is greater than 120% of the pre-exposure baseline.

FIG. 10 shows the resistive response of a micro-hotplate based $H_2$ gas sensor. The measurement was made in a 2-wire configuration, and the micro-hotplate was held at an elevated temperature by passing current (<5 mA) through the embedded polysilicon heater. In this experiment, the sensor was cyclically exposed 10 times to 0.25% $H_2$ in dry air.

Figure 11:
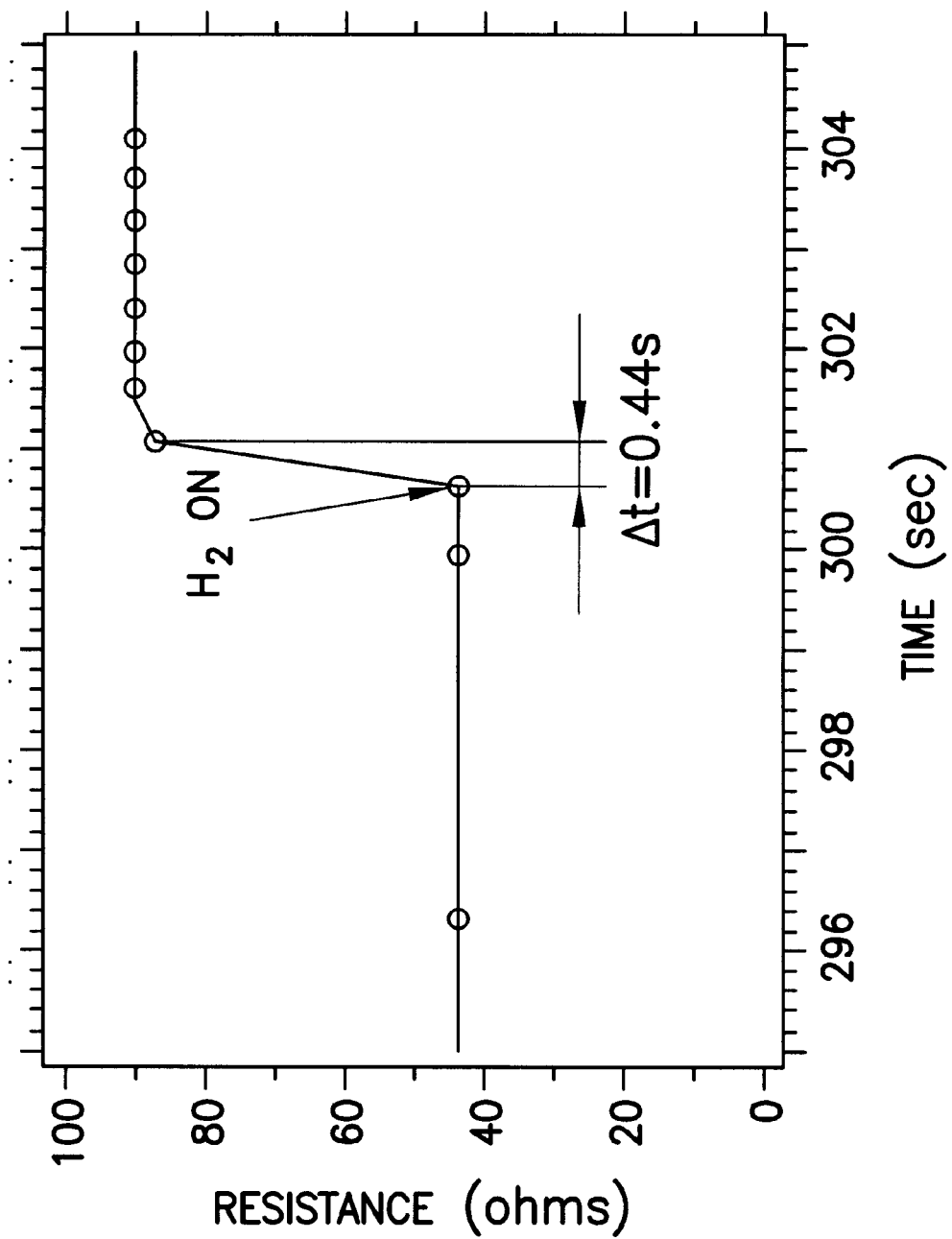
FIG. 11 provides an expanded scale plot of the resistive response of a micro hotplate based $H_2$ gas sensor to exposure to 0.25% $H_2$ in air, with a demonstrated speed of response <0.5 sec.

FIG. 11 focuses on the transition of one particular cycle with an expanded scale. In FIG. 11, a rise time of <0.44 s was measured. It should also be noted that the magnitude of the response was greater than 120%. This can be compared with the typical change in response of palladium alloy resistors, which is on the order of 10% when exposed to 1 atm of $H_2$.

Figure 12:
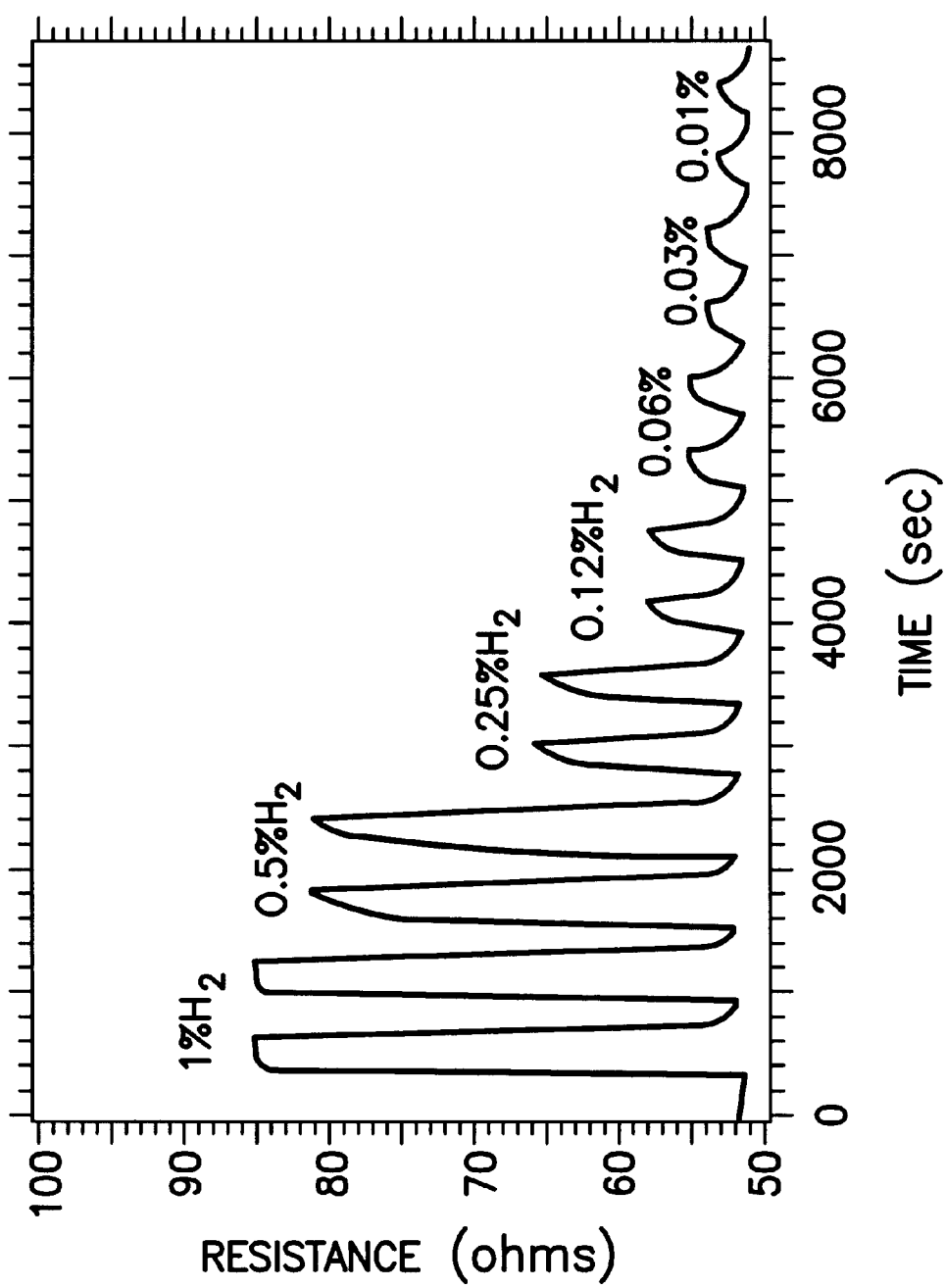
FIG. 12 plots the resistive response of a micro hotplate based $H_2$ gas sensor to concentrations of $H_2$ in air ranging from 1% to 0.01%.

FIG. 12 shows the response of a micro hotplate to different concentrations of $H_2$. In this experiment, the initial concentration was 1%, and it was decreased by a factor of 2 with each step until a final concentration of ~0.01% (150 ppm) was reached. The sensor was exposed two times at each concentration. The exposure time was 300 s and the time between exposures was also 300 s. The sensor exhibited detectable responses to nearly two orders of magnitude of $H_2$ concentration. The temperature of the hotplate was not intentionally varied in this experiment. It seems likely that the minimum detectable gas concentration can be further improved by optimizing the operation conditions at lower $H_2$ concentrations.

Figure 13:
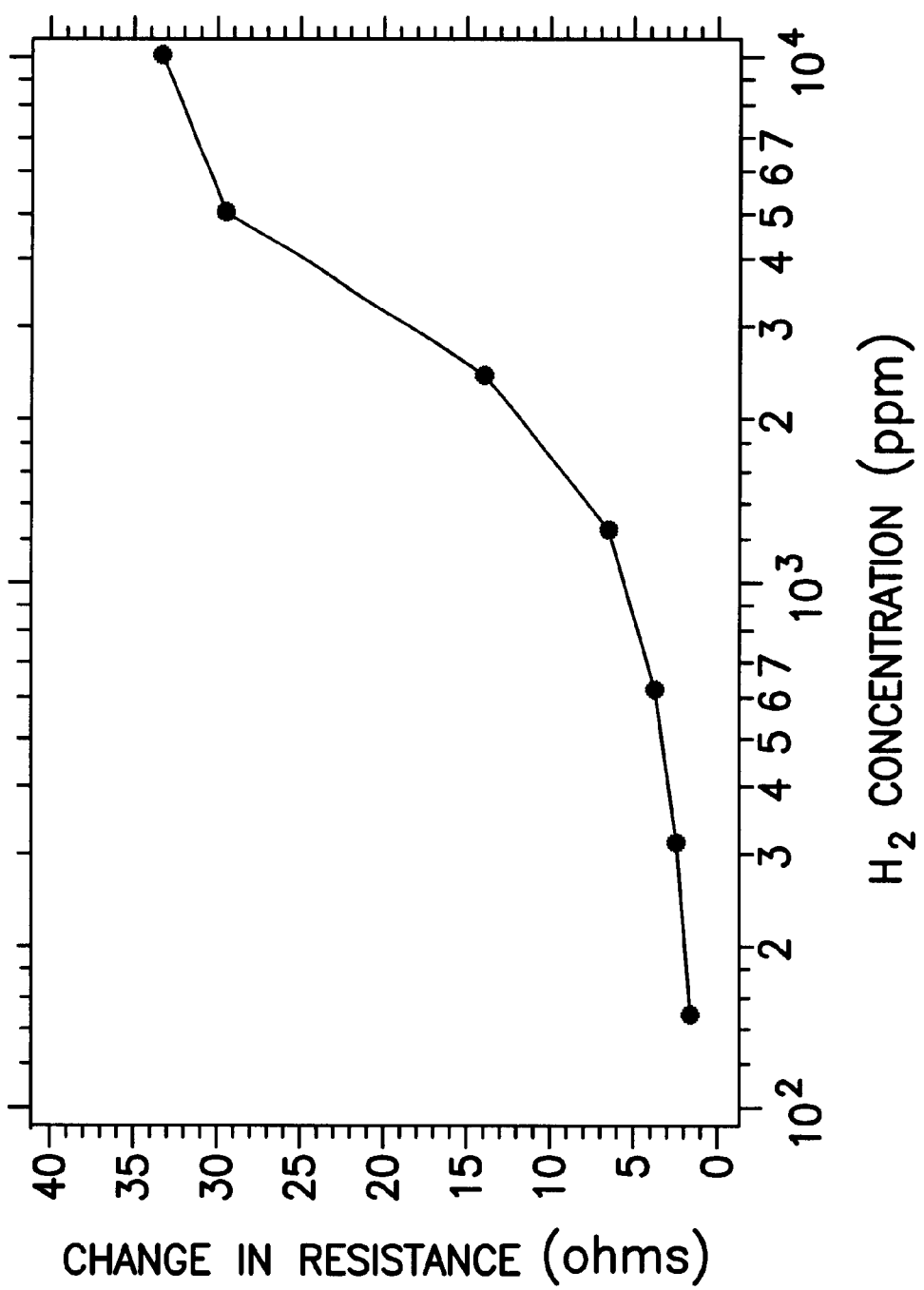
FIG. 13 plots the resistive response from the previous FIGURE, plotted as function of $H_2$ gas concentration.

FIG. 13 is a plot of the responses from FIG. 12 as a function of $H_2$ concentration. For this plot, the response was taken as the absolute change in resistance as measured from the beginning base line resistance. The $H_2$ concentration is plotted on a logarithmic axis, and shows that the response does not follow a simple dependence on the $H_2$ concentration. The reasons for the behavior of the resistivity as a function of $H_2$ are not currently well understood. One factor influencing the behavior of the curve in FIGURE is the fact that at the lower $H_2$ concentrations, the films response does not appear to have come to equilibrium within the exposure time. In addition to this, the influence of contact resistance in a two probe configuration should be considered. Further testing is required to obtain a more accurate understanding of this behavior.

Figure 14:
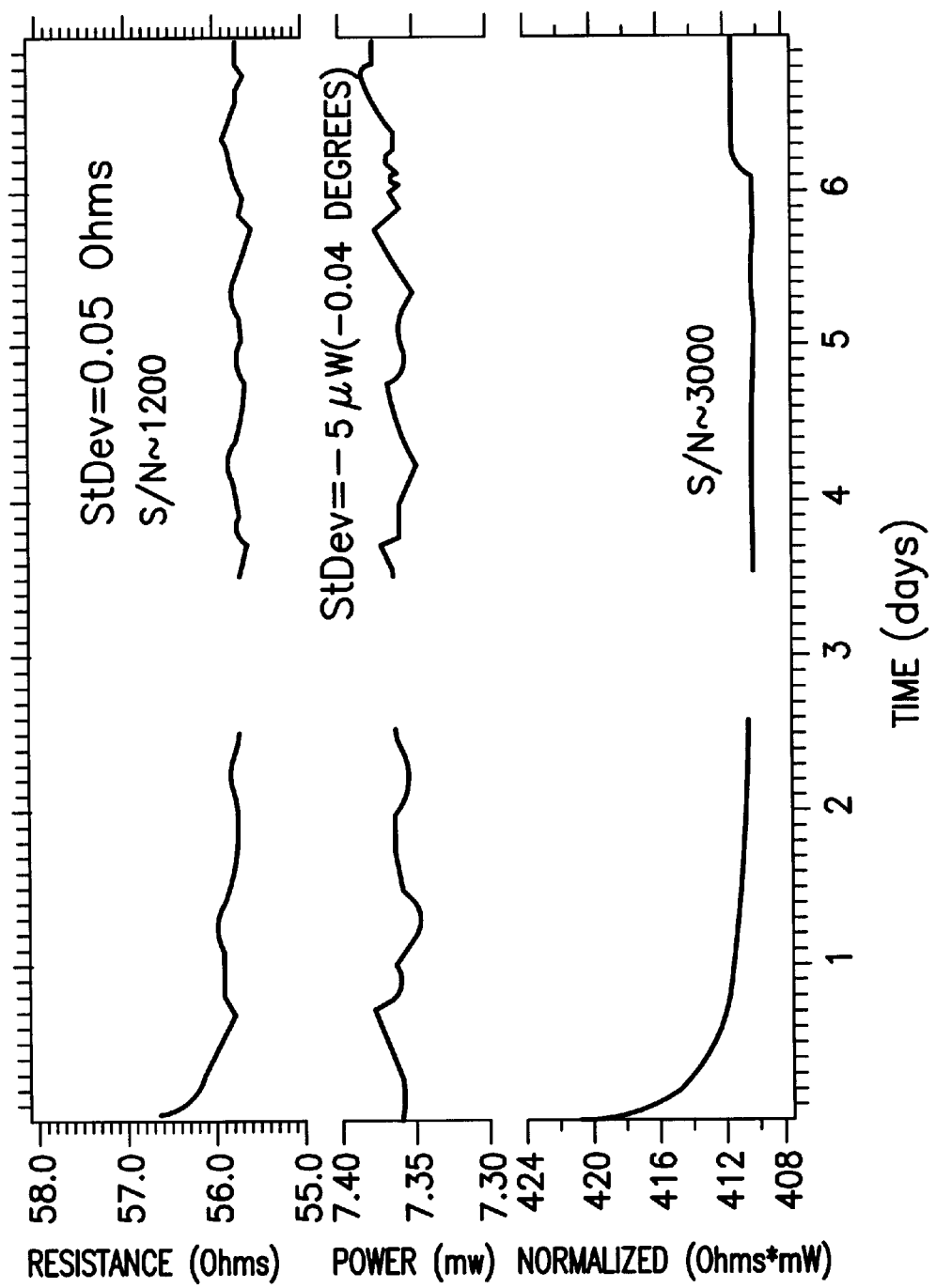
FIG. 14 plots stability results over a 7-day time frame.

Stability is an important requirement of any type of sensor. To begin the investigation in this area, the resistance as a function of time without $H_2$ exposure was examined for a period of several days in dry air, as shown in the top panel of FIG. 13. There was no flow over the sensor at this time. During the first day or so there is a small steady reduction in resistance, which eventually leveled out. This small drift was on the order of an ohm, which represents hydrogen in the sub-200 ppm range, and may either be due to outgassing from the sensing film, or from the chamber wall. After this, the resistance reached steady state, with a standard deviation of ~0.05 ohms. This resulted in a signal to noise ratio of ~1200 (average value/standard deviation). The middle panel of FIG. 14 shows the power consumed by the polysilicon heater element of the micro hotplate over the same time frame, which is expected to representative of the operating temperature. There appeared to be cyclical variation in the power, which has a ~24 hour period, i.e. a day/night difference. When the resistance is multiplied by the power consumed, which, to first order, compensates for temperature, the variation appears much reduced. The signal to noise now increases to nearly 3000, and a jump in resistance on day 6, which was lost in the noise, becomes noticeable.

The previously described MEMS based hydrogen gas sensors that couple a MEMS structure, a microhotplate, with a hydrogen sensitive coating made of palladium capped yttrium dihydride. This device has demonstrated capabilities as a Hydrogen sensor, with sensitivity to as little as 200 ppm of $H_2$ in dry air, and speeds of response of less than 0.5 s. However, there is a need to detect additional gases such has $NH_3$ and sulfur-containing compounds. Methods, thin film materials, and and systems for use with microhotplate based devices for these applications are described as follows:

There are several materials systems for detecting $NH_3$, vis a vis a microhotplate structure. These include:

a) The first method is based on the use of the Pd coated metal hydride film system that has successfully been used for the detection of hydrogen. This modifies the Pd/Metal Hydride film stack by adding an additional $NH_3$ catalyst layer to the surface. This layer which would be only on the order of a few monolayers or less, and then induces the disassociation of the $NH_3$ into $H_2$ and $N_2$, whereby the $H_2$ would then diffuse into the hydride layer and be detected as a resistance change. The catalyst may be selected from W, Pt, Rh, an alloy or combination of those or any other metal or material that lowers the disassociation temperature of $NH_3$ to within the operating range of the microhotplate, <550° C.

Another approach is to use metal stable sulfides, such as $Cu_2S$, AgS, and AuS as the $NH_3$ sensitive layer. In this approach, thin films of Cu, Ag, Au or potential other nobel metal sulfides (Pt, Pd, or Ir) are deposited on the microhotplate structure, and sulfides are formed via exposure to $H_2S$. These sulfides are then expected to exhibit a measurable change in resistance upon exposure to $NH_3$. This has been demonstrated for CuS and is extended here in the other metals mentioned. This concept is also novel for use of these with thin films on a microhotplate structure.

Yet another method is to use an acidic conducting polymer such as polyaniline and/or polythiophenes. In these materials, the adsorption of the basic gas $NH_3$ would change the conductivity level of the polymer thin film. This polymer film could be made as a high surface area polymer to increase the signal levels. It should be noted that the response times of the sensors demonstrated by Hirata et al are difficult to ascertain, but it is likely that substantial improvement is possible by thermal activation using the Microhotplate structure. Thermal profiles as a function of time would be chosen to avoid degrading the polymer coating. It is expected that the recovery time on removal of $NH_3$ would also be enhanced by thermal activation. Again the use of the microhotplate for temperature control is new and novel, especially in conjunction with these thin film layers The second method for detecting sulfides is based on the use of ultrathin metal films (<50 nm) of Rh, Ir and the like. These materials have been chosen because they are inert, have very low energies of oxide formation, and are known to form sulfur complexes. In addition, films of Pt, and Pd may be used either alone or as alloying compounds. Other materials that can be induced through heating to reversibly form a sulfide would also be candidates. Materials such as Ag, Cu and Au are candidates for instance, because although they are known to form quite stable sulfides, the addition of a catalyst or an alloy form may lead to a reversible sulfur reaction. It is also possible that nano-sized grains would be beneficial to the reversibility of sulfide formation, leading to a more versatile sensor technology. Addition candidate metals include, but are not limited to, Cd, Zn, Pb, Sb, and Bi.

Hydrogen containing gases such as $CH_4$, $C_2H_6$, acetone, methanol etc. are used in large variety of industrial applications ranging from semiconductor thin film processing to petroleum and polymer manufacturing. The combustible nature of many of these gases as well as the always increasing need for improved process control makes the detection and monitoring of these gases vitally important. Difficulties with the sensors that are currently used to detect these gases are that they are not chemically specific, and often will have similar response for different gases. In addition, many of these sensors are combustion based and rely on the presence of oxygen. It is desirable to have a sensor that will be reproducible and specific to individual hydrogen containing gases, and will be able to operate in environments with little to no oxygen present. It is also desirable to have a solid state sensor that has no moving parts, has a response time on the order of seconds, would operate with minimum power consumption, does not require frequent calibration, and could be used in a hand held portable instrument This embodiment combines the use of a catalytic layer on top of a rare earth hydride micro-hotplate gas sensor array. The rare earth hydride micro-hotplate sensor has been demonstrated to be extremely sensitive to hydrogen in an oxygen free environment, FIG. 1. The present invention seeks to exploit this sensitivity to hydrogen for the detection of hydrogen containing compounds. Temperature sensitive catalysis can be used to decompose hydrogen-containing compounds, thus releasing molecular or atomic hydrogen. This can then be detected by the rare earth hydride sensing films. By monitoring both the resistive response of the hydride thin films and the reaction temperature, specific gases can be identified. There is also the possibility of detecting low concentrations of $H_2O$ by looking for catalytically disassociated hydrogen with this method as well.

Figure 15:
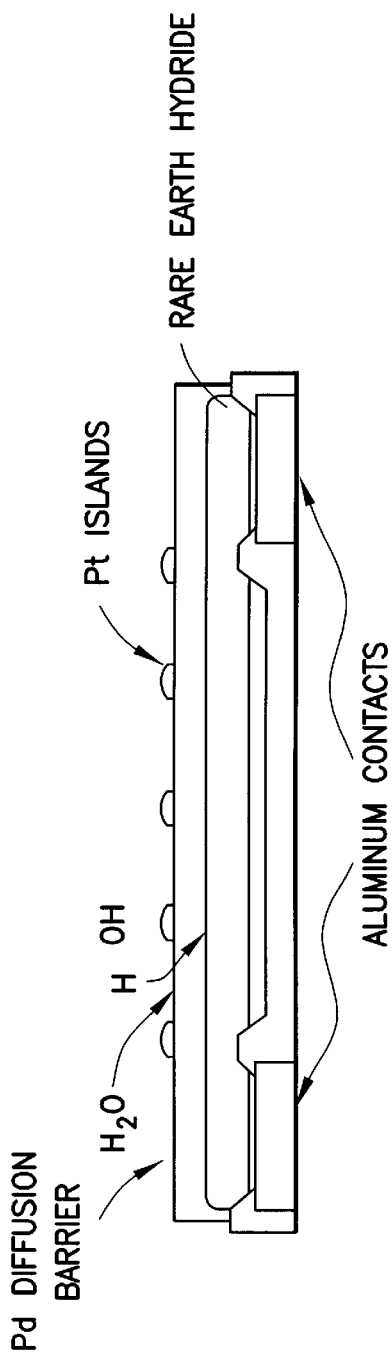
FIG. 15 provides a schematic diagram of platinum islands on palladium coated metal hydride active layer. In this diagram, the disassociation of water is used as an example.

There are several potential detection schemes or embodiments of the present invention. The first is the deposition of non-continuous catalytic islands (e.g. platinum) on top of the palladium/yttrium layers that will act the hydrogen sensor. In this configuration, as shown in FIG. 15 hydrogen released from the parent molecule at the platinum surface will be immediately available at the palladium surface for detection. One potential draw back to this is that the detection temperature must be the same as the catalysis temperature, which may not necessarily be simultaneously optimized.

Figure 16:
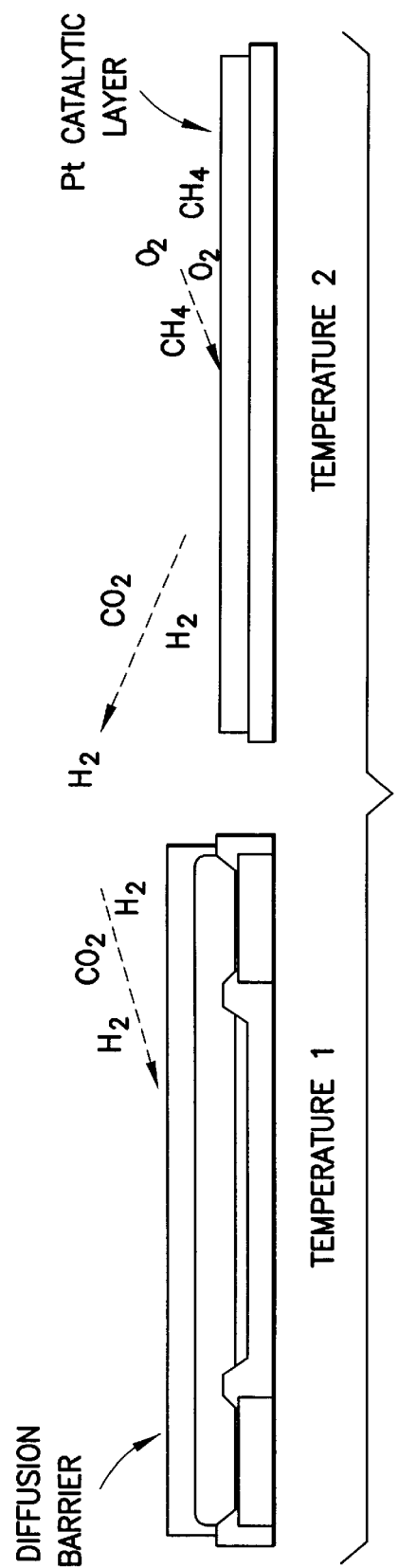
FIG. 16 provides a schematic diagram of separate catalytic and sensing hotplate devices operated in tandem to detect catalytically disassociated hydrogen for $CH_4$ as an example.

An alternative approach is shown in FIG. 16, wherein the catalytic reaction proceeds independently of the sensing by using an adjacent catalyticlly coated hotplate. In this approach, hydrogen released from the catalytic hotplate would diffuse or drift to the sensing hotplate, where it would be detected. In this way, each hotplate could be operated at the optimum temperature required for both the decomposition and detection. In addition, fabricating these adjacent hotplates without aluminum would allow temperatures as high as 800° C. to be used for catalysis. Currently fully functional hotplates with aluminum can not be operated above 500° C.

The present invention involves depositing Pd coated Y, La or other RE hydride films on the micro-hotplate structure, as well as the deposition of catalytic layers. The film fabrication may be accomplished either by physical vapor deposition methods or by chemical vapor deposition methods. If CVD is used, then the possibility exists that the separate heating of individual micro-hotplates can be used to develop a self-lithographic process.

One embodiment of the sensor fabrication would consist of the following steps. The desired micro-hotplate array would be designed and laid out, and might consist of 4, 8 or more individual elements. This would then be fabricated in a commercial CMOS process using a facility such as the MOSIS system. This would be micromachined and packaged. The packaged chip would be placed in either a PVD or a CVD chamber and the thin metallic films deposited on the hotplates. With the appropriate electrical feedthroughs, the hotplates can be heated to improve the properties of the metal film deposition. Also with the appropriate electrical feedthroughs, the resistance of the deposited films can be monitored in situ and used as feedback for the deposition process. For example when a certain conductance is reached, the film will be so thick and this conductance value can be used to stop the growth at this desired thickness. This will work for the RE and the Pd metallic over layers as well as the catalytic layers.

Another embodiment would follow the same basic steps as above with the exception that a non-commercial process might be used to fabricate the micro-hotplate instead of the CMOS process. Such non-commercial process might substitute Pt or W for the Al metallization typically used.

In either embodiment, Pd, RE, and catalytic films of different thickness within the same array can be used to cover a broader dynamic range of detection. For example, a thin film of Pd can be used to detect low concentrations of hydrogen. A thicker film of Pd can be used to detect higher concentrations, because it will be take more a concentration driving force for the diffusion o hydrogen through the thicker layer.

In addition, in either embodiment, experiments can then be conducted to determine the optimal operation temperature or temperatures. Because of the rapid thermal rise and fall time of the micro-hotplate, pulsed temperature operation can be considered. For example, the films might be most sensitive to initial hydrogen exposure at one temperature, but need a higher temperature to be returned to their initial state. The sensor could then be pulsed periodically to be refreshed, thus minimizing the effect of drift and improving long term stability.

The features and advantages of the present invention are more fully shown by the following non-limiting examples.

EXAMPLE 1

Thin Film Deposition of Yttrium by Physical Vapor Deposition

Vacuum refined yttrium lumps (99.9%) and palladium pellets (99.9%) were melted in an electron beam PVD tool and used as targets. Depositions were carried out on polished, high grade, quartz photomask blanks. A deposition methodology was established by trial and error that ensured the exclusion of oxygen and moisture in the deposition chamber. A 150 Å thick layer of Pd was determined to be necessary to protect the sensory yttrium layer.

An AFM topographical image of one of the films showed that the root mean square (RMS) roughness of the Pd protective over layer was 10.8 nm which was more than that of the film grown by CVD (2.5 nm). The $R_{max}$ of the film grown by PVD was also more than that of the film grown by CVD. Nevertheless, films grown by PVD are visibly smooth and reflective, in relation to the films grown by CVD.

EXAMPLE 2

Effects of Exposure of Rare Earth Metal Thin Films to Hydrogen

Strips of rare earth metal thin films were placed in a 1-inch diameter quartz CVD tube and exposed to slightly less than one atmosphere (700 Torr) of hydrogen. The color of the film turned yellowish within 2–3 minutes, indicating the permanent conversion of Y to $YH_2$. Within a minute of this color change the film displayed a striking change in optical transmission, changing from opaque and reflective to transparent. This optical change is reversible and provides a reversible hydrogen sensor. Upon removal of hydrogen an immediate loss of transparency was noted although complete opacity was restored after only several hours. This demonstrates the suitability of rare earth metal thin films for inexpensive, hydrogen-specific, optical sensors in accordance with the present invention.

EXAMPLE 3

Hydrogen Selectivity of Rare Earth Metal Thin Films

A series of film growth experiments was carried out to determine the effect of film thickness both on stress and on the sensory properties of the film. Three sets of films (4 each) with yttrium thicknesses of 2500, 4000 and 5000 Å were grown. Each film had a 150 D Pd protective over layer deposited thereon.

The selectivity of the sensor was demonstrated by optical change from opaque to clear when the films were exposed to:

1) hydrogen diluted in 50% nitrogen;
2) hydrogen-saturated pentane vapors, thereby presenting hydrogen to the sensor in a low boiling organic solvent; and
3) hydrogen diluted with 50% ammonia.

These results demonstrated the selectivity of the sensor of the present invention. We are unaware of any commercially available sensor that can detect hydrogen under any of the above conditions (1)–(3).

EXAMPLE 4

Fabrication and Testing of Rare-Earth Coated Microhoplate $H_2$ Gas Sensor

Micro hotplate structures were fabricated through a commercial foundry and the as-received die was micro machined using $XeF_2$ as a silicon selective etchant. A photolithographic lift-off process was used in combination with physical vapor deposition (PVD) to sequentially deposit yttrium thin films overlaid by palladium on the suspended micro hotplate structures. Vacuum refined yttrium lumps (99.9%) and palladium pellets (99.9%) were melted in an electron beam deposition tool and used as targets. The EDS spectrum of the films clearly indicated the presence of both yttrium and palladium on the microhotplates. These devices were wirebonded and packaged in 40 pin ceramic chip carriers.

The fully packaged chips were placed in a sealed chamber, and electrical contact made via feed-throughs into the chamber. Nitrogen and hydrogen were introduced into the chamber and controlled with mass flow controllers and actuated valves. The resistance of the sensing film was measured periodically with a digital multimeter and logged on a desktop computer. A DC power supply was used to heat the microhotplates. It was found that these devices have a significant resistive response to hydrogen in the absence of oxygen. Both the magnitude and speed of this response was found to depend on temperature, thus indicating the value of the micro-hotplate platform. Changes in resistance of greater than 110% were observed in hydrogen concentrations of 3%. Extrapolation of responses measured over a decade of hydrogen concentrations, (0.1%–3%) suggests that better than 100 ppm sensitivity is achievable. The lowest rise and fall times measured were 30 and 300 s respectively.

A significant advantage provided by the present invention is that the micro hotplate based approach for $H_2$ gas sensing is based on commercially available semiconductor processing technology. This technology is readily accessible though a number of integrated chip foundry facilities. The small size and simplicity of the micro-hotplate device can further leverage this advantage, and we therefore estimate that more than 1 million devices could be produced on a single lot of 25 six-inch wafers. Analysis further indicates that at these quantities, the final device cost becomes dominated by the packaging costs.

These sensors have shown exceptional responsivity. Changes in resistance of >120% to 0.25% $H_2$ concentrations have been measured, with response times <0.5 sec. These sensors have demonstrated a dynamic range of two orders of magnitude, detecting $H_2$ from >200 ppm to >1%. In the area of stability, we have demonstrated an un-corrected baseline signal to noise ratio of ~1200, and a temperature compensated signal to noise of ~3000. From a commercialization standpoint, our preliminary analysis indicates that this technology is readily scalable to quantities >1 million devices. These results are extremely encouraging and suggest that this technology has substantial potential for meeting the sensing requirements of a hydrogen based energy economy.

The present invention provides another benefit, in that MEMS based gas sensors may be produced via a CMOS foundry process. Several laboratories have described the realization of such micro-machined suspended structures via a CMOS foundry process. First micro-hotplate device structures may be designed using available CAD layout software packages and fabricated through foundry service. Next, as-received chips are etched using $XeF_2$ or other known processes to create suspended micro-hotplate device structures. The functionalization step involves applying a $H_2$ sensitive coating to the surface of structures. The precise nature of both the materials and deposition can be thought of as a rare-earth based film, overcoated with a palladium-based layer. The final fabrication step is to dice and package the solid-state sensors.

While the invention has been described herein with reference to various illustrative aspects, features and embodiments, it will be recognized that the invention is not thus limited, but rather encompasses numerous other variations, modifications and other embodiments, as will readily suggest themselves to those of ordinary skill in the art, based on the disclosure and examples herein. Accordingly, the invention is to be broadly construed and interpreted, with respect to the ensuing claims, as including all such variations, modifications and other embodiments within its spirit and scope.

What is claimed is:

1. A hydrogen sensor, comprising:
   at least one hydrogen-interactive thin film sensor element comprising a rare earth metal or a rare metal dihydride, arranged for exposure to an environment susceptible to the incursion or generation of hydrogen, wherein said rare earth metal or rare earth metal dihydride exhibits a detectable change of physical property when exposed to hydrogen;
   at least one micro-hotplate structure coupled to said hydrogen-interactive sensor element for selective heating of the sensor element;
   a hydrogen-permeable material overlaying each hydrogen-interactive element for selective permeation of hydrogen, wherein said hydrogen-permeable material comprises an alloy to suppress a phase change therein; and
   a detector constructed and arranged for detecting said detectable change of physical property exhibited by said rare earth metal or rare earth metal dihydride upon exposure to hydrogen.

2. The hydrogen sensor of claim 1, wherein said alloy comprises at least: (1) a first element selected from the group consisting of palladium, platinum, iridium, ruthenium, silver, gold, cobalt, and alloys thereof, and (2) a second element selected from the group consisting of silver, titanium, nickel, chromium, aluminum, and alloys thereof.

3. The hydrogen sensor of claim 1, wherein said alloy comprises at least one element selected from the group consisting of titanium and nickel.

4. The hydrogen sensor of claim 1, wherein said detectable change of physical property is selected from the group consisting of optical transmissivity, electrical resistivity, electrical conductivity, electrical capacitance, magnetoresistance and photoconductivity.

5. The hydrogen sensor of claim 1, wherein said detector is constructed and arranged to convert said detectable change of physical property to a perceivable output selected from the group consisting of visual outputs, auditory outputs, tactile outputs, and auditory outputs.

6. The hydrogen sensor of claim 1, wherein said alloy comprises palladium-silver alloy containing more than about 10% silver by total weight.

7. The hydrogen sensor of claim 1, wherein the hydrogen-interactive thin film sensor element comprises at least one thin film layer comprising one or more metals, present in elemental metal form and/or in a dihydride thereof, wherein the metal is selected from the group consisting of:

magnesium, calcium, strontium, barium, scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys thereof.

8. The hydrogen sensor of claim 1, wherein said alloy comprises palladium-silver alloy containing about 20% silver by total weight.

9. The hydrogen sensor of claim 1, wherein said detectable change of physical property comprises a change of electrical conductivity or resistance.

10. The hydrogen sensor of claim 1, wherein said alloy comprises palladium and at least one element selected from the group consisting of silver, titanium, nickel, chromium, and aluminum.

11. The hydrogen sensor of claim 1, wherein the hydrogen-interactive thin film sensor element comprises a rare earth metal thin film that is doped with a dopant.

12. The hydrogen sensor of claim 1, wherein the micro-hotplate structure is controlled by a predetermined time-temperature program for cyclic heating of the hydrogen-interactive thin film gas sensor element by the micro-hotplate structure.

13. The hydrogen sensor of claim 1, wherein said hydrogen-interactive thin film has a thickness of from about 50 to about 2000 nm.

14. The hydrogen sensor according to claim 1, wherein the hydrogen-permeable thin film has a thickness of from about 2 to about 1000 nm.

15. The hydrogen sensor according to claim 1, comprising a plurality of hydrogen-interactive thin film sensor elements.

16. The hydrogen sensor of claim 1, wherein the hydrogen-interactive thin film sensor element is formed of a material consisting essentially of rare earth metal dihydride of one or more trivalent rare earth metals, wherein said rare earth metal dihydride is reversibly reactive with hydrogen to form corresponding metal trihydride exhibiting a detectable change of physical properties.

17. The hydrogen sensor of claim 1, wherein said alloy comprises palladium-silver alloy.

18. The hydrogen sensor of claim 17, wherein said palladium-silver alloy is formed by the steps comprising:

separately depositing at least one palladium layer and at least one silver layer on the hydrogen-interactive thin film sensor element; and annealing said palladium layer and said silver layer, so as to form the palladium-silver alloy.

19. The hydrogen sensor of claim 18, wherein the annealing is conducted at a temperature that is above about 250° C. and below melting points of either of palladium and silver.

20. The hydrogen sensor of claim 1, wherein the hydrogen-interactive thin film sensor element comprises yttrium, and the physical property change comprises a change of electrical conductivity or resistivity when the hydrogen-interactive thin film sensor element is contacted with hydrogen gas.

21. The hydrogen sensor of claim 20, wherein said dopant is selected from the group consisting of magnesium, calcium, strontium, barium, and any combination thereof.

22. The hydrogen sensor of claim 21, wherein said dopant is deposited on the hydrogen-interactive thin film.

23. The hydrogen sensor of claim 1, wherein the hydrogen-permeable material is in the form of a thin film.

24. The hydrogen sensor according to claim 23, wherein at least two hydrogen-interactive thin film sensor elements are covered by hydrogen-permeable material of different thickness.

25. The hydrogen sensor according to claim 23, wherein at least two hydrogen-interactive films comprises different materials.

26. A method of fabricating a hydrogen sensor on a substrate, comprising:

constructing on the substrate a micro-hotplate structure; and forming on the micro-hotplate structure a hydrogen-interactive thin film comprising a rare earth metal and/or a rare earth metal dihydride that upon exposure to hydrogen exhibits a detectable change of at least one physical property, and wherein the hydrogen-interactive thin film is arranged to be heated by the micro-hotplate structure; and forming on the hydrogen-interactive thin film a protective over layer comprising a hydrogen-permeable material for selective permeation of hydrogen, wherein said hydrogen-permeable material comprises an alloy to suppress a phase change in said rare earth metal or rare earth metal dihydride.

27. The method of claim 26, wherein said alloy comprises at least one element selected from the group consisting of silver, titanium, nickel, chromium, and aluminum.

28. The method of claim 26, further comprising coupling the hydrogen-interactive thin film with a detector for outputting the detectable change of physical property of the hydrogen-interactive thin film when the hydrogen-interactive thin film is exposed to hydrogen.

29. The method of claim 26, wherein the alloy comprises at least one element selected from the group consisting of titanium and nickel.

30. The method of claim 26, wherein the hydrogen-interactive thin film comprises one or more metal components, in elemental metal form and/or in a corresponding metal dihydride selected from the group consisting of:

magnesium, calcium, strontium, barium, scandium, yttrium, lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium, lawrencium, and alloys containing one or more of such metals.

31. The method of claim 26, wherein the hydrogen-permeable material comprises a metal selected from the group consisting of palladium, platinum, iridium, silver, gold, cobalt, and alloys thereof.

32. The method of claim 26, wherein the hydrogen-interactive thin film is doped with a dopant.

33. The method of claim 26, wherein the hydrogen-interactive thin film comprises yttrium, formed on the substrate by chemical vapor deposition utilizing as a precursor Y(NSiMe$_3$)$_3$.

34. The method of claim 26, wherein said alloy comprises palladium-silver alloy containing more than about 10% silver by total weight.

35. The method of claim 36, wherein said alloy comprises palladium-silver alloy containing about 20% silver by total weight.

36. The method of claim 26, wherein said alloy comprises palladium and at least one element selected from the group consisting of silver, titanium, nickel, chromium, and aluminum.

37. The method of claim 26, wherein said alloy comprises palladium-silver alloy.

38. The method of claim 37, wherein said palladium-silver alloy is formed by the steps comprising:
   separately depositing at least one palladium layer and at least one silver layer on the hydrogen-interactive thin film; and
   annealing said palladium layer and said silver layer, so as to form the palladium-silver alloy.

39. The method of claim 26, further comprising coupling the hydrogen-interactive thin film with an electrical resistance monitor to provide an output indicative of the presence of hydrogen in an environment in contact with the rare earth metal thin film.

40. The method of claim 39, wherein the dopant is deposited on the hydrogen-interactive thin film from a precursor, and said precursor is selected from the group consisting of Mg(thd)$_2$, Ca(thd)$_2$, dimethyl aluminumhydride, Ba(thd)$_2$, Sr(thd)$_2$, (COD)Ir(hfac) and Co(thd)$_2$.

41. The method of claim 26, wherein the hydrogen-interactive thin film comprises a metal selected from the group consisting of lanthanum and yttrium, and the hydrogen-interactive thin film is formed on the substrate by chemical vapor deposition utilizing a corresponding precursor, wherein said precursor is selected from the group consisting of tris(cyclopentadienyl)lanthanum, tris(cyclopentadienyl)yttrium, β-ketoamine complexes of lanthanum, β-ketoamine complexes of yttrium, β-diketonate complexes of lanthanum, β-diketonate complexes of yttrium, β-diiminate complexes of lanthanum, β-diiminate complexes of yttrium; lanthanum amides, and yttrium amides.

42. The method of claim 4, wherein the annealing is conducted at a temperature that is above about 250° C. and below melting points of either of palladium and silver.

43. A hydrogen sensor, comprising:
   at least one hydrogen-interactive thin film sensor element comprising a rare earth metal or a rare metal dihydride, which exhibits a detectable change of physical property when exposed to hydrogen;
   a hydrogen-permeable material overlaying each hydrogen-interactive element for selective permeation of hydrogen, wherein said hydrogen-permeable material comprises an alloy containing at least one metal element selected from the group consisting of titanium and nickel; and
   a detector constructed and arranged for detecting said detectable change of physical property exhibited by said rare earth metal or rare earth metal dihydride upon exposure to hydrogen.

* * * * *